(12) United States Patent
Gabrielsson

(10) Patent No.: US 8,932,855 B2
(45) Date of Patent: Jan. 13, 2015

(54) IMMUNE MODULATING EXOSOMES

(75) Inventor: Susanne Gabrielsson, Åkersberga (SE)

(73) Assignee: ITH Immune Therapy Holdings AB, Stockholm (SE)

( * ) Notice: Subject to any disclaimer, the term of this patent is extended or adjusted under 35 U.S.C. 154(b) by 32 days.

(21) Appl. No.: 13/381,429

(22) PCT Filed: Jul. 2, 2010

(86) PCT No.: PCT/EP2010/003946
§ 371 (c)(1),
(2), (4) Date: Mar. 23, 2012

(87) PCT Pub. No.: WO2011/000551
PCT Pub. Date: Jan. 6, 2011

(65) Prior Publication Data
US 2012/0183575 A1 Jul. 19, 2012

(30) Foreign Application Priority Data
Jul. 2, 2009 (SE) .................................. 0900904

(51) Int. Cl.
C12N 5/08 (2006.01)
C12N 5/00 (2006.01)
C12N 5/02 (2006.01)
A61K 39/00 (2006.01)

(52) U.S. Cl.
CPC .............. A61K 39/0011 (2013.01); A61K 39/00 (2013.01); A61K 2039/51 (2013.01); A61K 2039/5154 (2013.01); A61K 2039/5156 (2013.01); A61K 2039/55516 (2013.01)
USPC .......... 435/372.2; 435/375; 435/377

(58) Field of Classification Search
None
See application file for complete search history.

(56) References Cited

U.S. PATENT DOCUMENTS

2006/0233750 A1   10/2006   Xiang

FOREIGN PATENT DOCUMENTS

WO   WO 99/64603 A2   12/1999
WO   WO 01/82958 A2   11/2001

OTHER PUBLICATIONS

Raposo et al ( J Exp. Med. 1996, v.183, pp. 1161-1172.*
Rialland et al., ( Biol Cell, 2006, v.98, pp. 491-501.*
Mignot et al., J cell Mol.Med 2006, v.10, pp. 376-388.*
Dukers et al ( J of Immunol, 2000,v.165, pp. 663-670.*
Hsu et al., J of Immunol, 2003, v.26, pp. 440-450.*
Mignot et al J Cell Mol. Med., 2006, v.10, pp. 376-388.*
Papp et al., "B lymphocytes and macrophages release cell membrane deposited C3-fragments on exosomes with T cell response-enhancing capacity," Molecular Immunology, vol. 45, pp. 2343-2351, 2008.
Qin et al., "Evidence for an Important Interaction Between a Complement-Derived CD21 Ligand on Follicular Dendritic Cells and CD21 on B Cells in the Initiation of IgG Responses," J. Immunol., vol. 161, pp. 4549-4554, 1998.
Raposo et al., "B Lymphocytes Secrete Antigen-presenting Vesicles," J. Exp. Med., vol. 183, pp. 1161-1172, Mar. 1996.
Flanagan et al., "Localization of the Epstein-Barr virus protein LMP 1 to exosomes," Journal of General Virology, vol. 84, pp. 1871-1879, 2003.
Olesen et al., "The requirement of localized, CR2-mediated, alternative pathway activation of complement for covalent deposition of C3 fragments on normal B cells," Immunology, vol. 93, pp. 177-183, 1998.
Skokos et al., "Mast Cell-Dependent B and T Lymphocyte Activation Is Mediated by the Secretion of Immunology Active Exosomes," The Journal of Immunology, vol. 166, pp. 868-876, 2001.
Qazi et al., "Antigen-loaded exosomes alone induce Th1-type memory through a B cell-dependent mechanism," Blood, vol. 113, No. 12, pp. 2673-2683, Mar. 19, 2009.
Middeldorp et al., "Multiple roles of LMP1 in Epstein-Barr virus induced immune escape," Seminars in Cancer Biology, vol. 18, pp. 388-396, 2008.
International Search Report issued on Nov. 17, 2010 in application No. PCT/EP2010/003946.

* cited by examiner

Primary Examiner — Michail Belyavskyi
(74) Attorney, Agent, or Firm — Ian J. Griswold; Johnson, Marcou & Isaacs, LLC

(57) ABSTRACT

A method of treating cancer in a patient comprises immortalizing B cells collected from the patient by infection with Epstein Barr virus, transforming the cells to a latent stage, culturing the cells in the presence of a cancer antigen, harvesting exosomes released from the cells, administering the exosomes to the patient. Alternatively the harvested exosomes are loaded with cancer antigen.

12 Claims, 13 Drawing Sheets

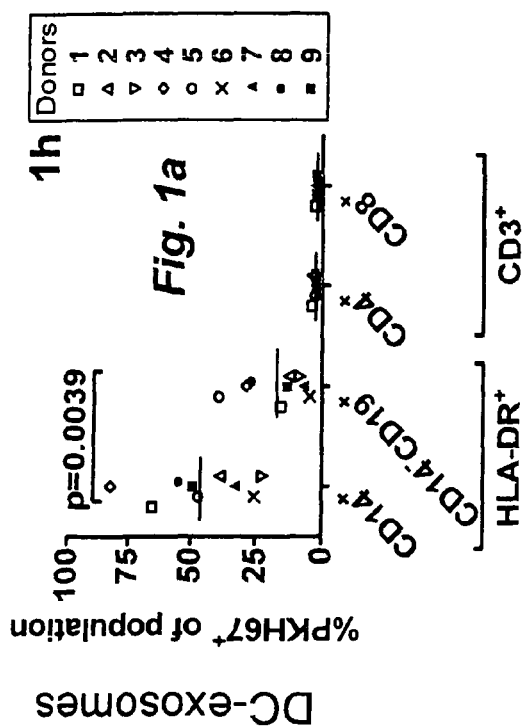
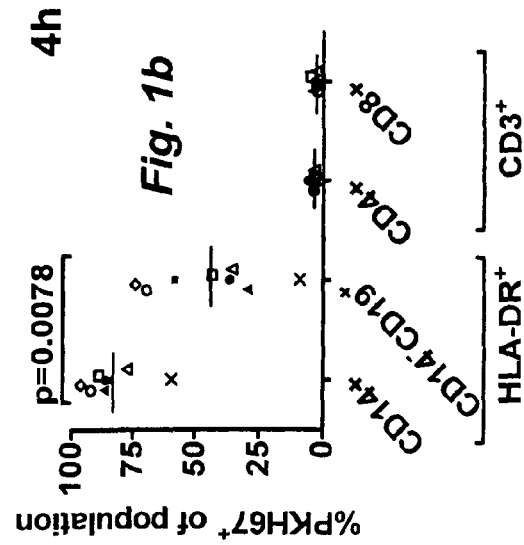
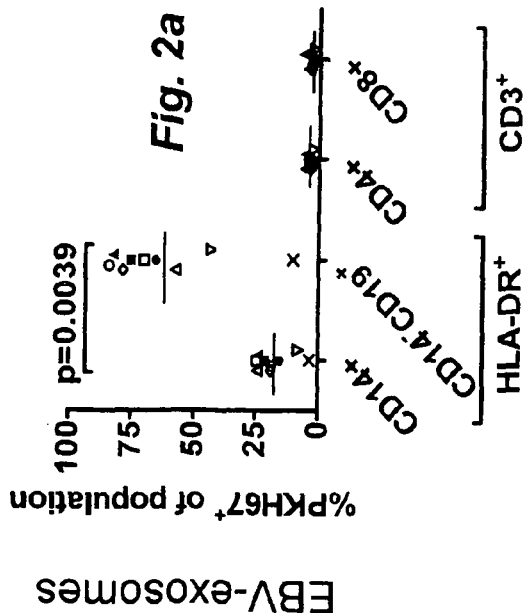
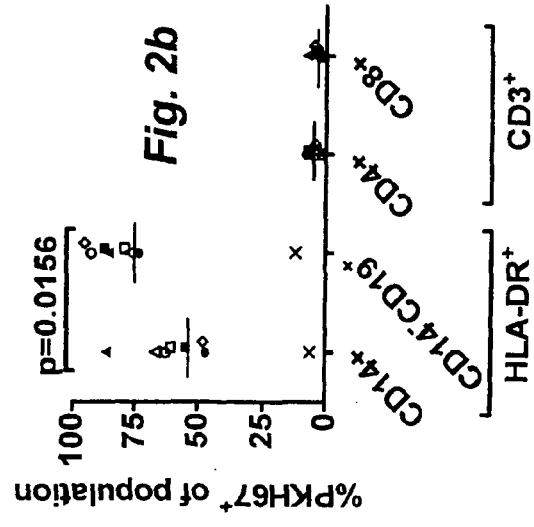

IMMUNE MODULATING EXOSOMES

FIELD OF THE INVENTION

The present invention relates to methods and a means for invoking an immunomodulary response in a subject by the use of exosomes derived from e.g. B-cells or dendritic cells. By the methods according to the invention enables treatment of cancer in a patient based using exosomes. More particularly the invention relates to a method of eliciting an immune response to an antigen displayed on a cancerous cell of the patient by means of an exosome. The invention also relates to the use of exosomes derived from e.g. B-cells to suppress an immune response which may be desirable in therapy during transplantation of any tissue.

BACKGROUND OF THE INVENTION

Cancer affects millions of people each year. While considerable progress in the treatment of cancer has been made over the last decades, better treatment is still in great need.

In the art there is a great number of chemical and biological agents of demonstrated or suggested use in the treatment of cancer, among them exosomes of human origin.

Exosomes are nano-sized vesicles which can carry antigen as well as co-stimulatory molecules. Dendritic cells (DC) are antigen-processing and antigen-presenting cells pertaining to the mammalian immune system. In a state activated by antigen they interact with B cells and T cells to trigger their adaptive immune response. During the last decade dendritic cell (DC) derived exosomes have been tested in animal models and clinical trials for the treatment of malignant disease. DC derived exosomes can stimulate T cell activation in vitro and in vivo, and eradicate tumors in mice (Amigorena S, *Anti-tumour immunotherapy using dendritic-cell-derived exosomes.* Res Immunol 1998, 149(7-8): 661-662; Zitvogel L et al., *Eradication of established murine tumors using a novel cell-free vaccine: dendritic cell-derived exosomes.* Nat Med 1998, 4(5): 594-600). Different cell types produce exosomes with phenotypes that reflect their cells of origin (Johansson S M et al., *Different types of in vitro generated human monocyte-derived dendritic cells release exosomes with distinct phenotypes.* Immunology 2008, 123: 491-499. Segura, et al., *Mature dendritic cells secrete exosomes with strong ability to induce antigen-specific effector immune responses.* Blood Cells Mol Dis 2005, 35: 89-93). The current dogma says that dendritic cell derived exosomes are preferred to B cell derived ones, since the corresponding cell, dendritic cell, is more efficient in stimulating naïve T cells compared to B cells. However, B cell exosomes have never been explored in this context.

A role for B cells in producing a complete T cell response has been suggested (Ron Y and Sprent J, *T cell priming in vivo: a major role for B cells in presenting antigen to T cells in lymph nodes.* J Immunol 1987, 138(9): 2848-2856). Lately, Ding et al. showed that targeting of antigens to B cells can potentiate specific T cell responses and break immune tolerance (Ding C et al., *Targeting of antigens to B cells augments antigen-specific T-cell responses and breaks immune tolerance to tumor-associated antigen MUC1.* Blood 2008, 112 (7): 2817-2825). Furthermore, new data show that B cells are particularly important in achieving long term T cell immunity (Whitmire J K et al., *Requirement of B Cells for Generating CD4+ T Cell Memory.* J Immunol 2009, 182(4): 1868-1876). Exosomes can carry B cell epitopes; B cell response is needed for T cell proliferation (Quazi K R et al., *Antigen loaded exosomes alone induce Th1 type memory through a B-cell dependent mechanism.* Blood 2009, 113:2673-2683). It is debated whether exosomes are able to stimulate T cells by themselves (Admyre C et al., *Direct exosome stimulation of peripheral human T cells detected by ELISPOT.* Eur J Immunol 2006, 36: 1772-1781) or if other cells are needed as intermediates (Vincent-Schneider H et al. *Exosomes bearing HLA-DR1 molecules need dendritic cells to efficiently stimulate specific T cells.* Int Immunol 2002, 14: 713-722) and antigen specificity may influence the direct interaction between exosomes and T cells. Exosomes of different origin target specific cell populations in human blood (Johansson S M et al., in: Johansson S M, *Exosomes—nano-vesicles in immune regulation.* Thesis for doctoral degree 2008, Karolinska Institutet, Stockholm, ISBN 978-91-7409-058-1.

Complement component (3d/Epstein Barr virus) receptor 2 (CD21; also: CR2) is a receptor on the surface of B cells involved in their activation and maturation.

Epstein-Barr virus (EBV) is a human lymphotropic herpes virus. EBV can immortalize primary B cells into lymphoblastoid cells that can be grown in vitro. EBV glycoprotein gp350 binding to CD21 is critical for viral attachment to B cells (Young K A et al., *Molecular basis of the interaction between complement receptor type 2 (CR2/CD21) and Epstein-Barr virus glycoprotein gp 350.* J Virol 2008, 82: 11217-11227). Exosomes from EBV-transformed B cells have been reported to carry the EBV-encoded latent membrane protein 1 (LMP1) which has a T-cell inhibitory activity (Keryer-Bibens C et al., *Exosomes released by EBV-infected nasopharyngeal carcinoma cells convey the viral latent membrane protein 1 and the immunomodulatory protein galectin 9.* BMC Cancer 2006, 6: 283).

SUMMARY OF THE INVENTION

The inventor of present invention have surprisingly found that EBV transformed B-cells excretes exosomes that specifically bind to the CD21 receptor of native B-cells mediated by protein gp350. Specifically, B-cells harboring EBV in its lytic stage produce exosomes binding to native B-cells. On the other hand the inventors have found that exosomes from human dendritic cells or breast milk target monocytes. Thus, in contrast to what has earlier been reported, the exosomes according to the invention may specifically target native B-cells or monocytes and thus not T-cells. Consequently, by producing exosomes according to the methods of the invention, the exosomes comprise a protein capable of specifically binding to the CD21 receptor of e.g. a native B-cell, and by further incorporating one or more antigens into the exosomes according to the invention a specific immune response may result upon contact of the exosomes with native B-cells acting as antigen presenting cells (APCs) in further recruitment of T-cells. In short, the exosomes according to the invention can be seen as comprising an anchor (in form of a protein) connecting to a native B-cell receptor and an antigen that is transferred to the native B-cell.

OBJECTS OF THE INVENTION

It is an object of the present invention to provide a method of treating cancer in a patient by activating the immune system of the patient by means of exosomes.

More particularly, an object of the present invention is to target a tumour antigen to provide a stimulatory signal to a B cell.

Another important object of the present invention is to provide a tumor antigen-presenting exosome in an amount sufficient for the treatment of cancer in a patient.

Thus present invention relates to i.a. exosomes derived from e.g. B-cells, wherein the exosomes carry an protein capable of binding to e.g. a B-cell receptor and wherein the exosomes also carry one or more antigens of any kind.

Present invention also relates to a method for targeting B cells by exosomes originating from other B cells, dendritic cells, monocytes or macrophages, wherein the exosomes carry an antigenic property capable of eliciting an immune response after binding to the targeting B-cell.

Present invention further relates to exosomes for use in treatment of diseases having their origin in immunomodulation or neoplasia, such as e.g. cancer and may further be useful in the context of infection, allergy, autoimmune diseases and further useful in therapy during e.g. transplantation, wherein exosomes according to the invention may be engineered to either elicit an immune response towards one or more antigens such as e.g a tumour antigen or alternatively, the exosomes according to the invention may be engineered to suppress an immune response as e.g. desired in the context of transplantation to avoid having transplanted tissue rejected by the subject's immune system.

Present invention also relates to a method for producing exosomes designed to target native B-cells.

Further objects of the invention will become evident from the following summary of the invention, the detailed description thereof illustrated by a number of figures, and the appended claims.

DESCRIPTION OF THE INVENTION

Methods of producing exosomes targeting B-cells

Present invention provides a method for producing specific immune modulating exosomes targeting B-cells, the method comprising the following steps:
(i) Transforming B-cells with suitable means, such as e.g. infecting said B-cells with Epstein Barr virus, to a latent stage to thereby express one or more moieties capable of binding to a native B-cell.
(ii) Culturing the transformed B-cells in (i),
(iii) Havesting the exosomes released from the transformed B-cells in (ii), wherein said exosomes comprise one or more moieties capable of binding to a native B-cell, and wherein the exosomes are directly and/or indirectly loaded with one or more antigens and/or immunosuppressing agents As indicated above, the exosomes may be loaded with one or more antigens by co-culturing the transformed B-cells (indirect loading) in (ii) with e.g. one or more antigens. On the other hand the method also allows for direct loading of the exosomes, i.e. after having harvested the exosomes in (iii) the collected exosomes as subjected to e.g. one or more antigens. Direct loading is usually performed with fragments of proteins such as peptides or peptide fragments such as e.g. peptide fragment comprising from 8 to 12 amino acid residues or from 15 to 24 amino acid residues. Alternatively, omitting indirect loading in (ii) necessitates loading in step (iv). Direct loading comprises contacting an EBTB exosome or a DC exosome with any antigen (one or more antigens of any kind independently of each other) under conditions promoting the uptake of the one or more antigens by the exosome. This may be e.g. under conditions comprising a shift in pH. This may be realized by suspending the exosomes in a suitable medium of a pH of at least pH 5, preferably about pH 5.2 at 4° C. Adding the peptide fragments and thereafter add a buffer such as e.g. TRIS-buffer to raise the pH to about pH 7.0 to thereby incorporate the peptide fragment to the exosome. There are also techniques for direct leading without the need to change the pH. However, it is also envisaged that multiple loading methods can be employed using both direct and indirect loading techniques. The inventors have found indirect loading to be particularly effective.

The one or more antigens may be endogenous/autogenic (coming from the subject itself) or exogenous/allogenic (coming from another subject) or in the case of more antigens being incorporated into/onto the exosomes the antigens may be any mix of autogenic/allogenic antigens. Preferably the antigens are autogenic. Moreover, the one or more antigens may have any origin such as e.g. viral or bacterial or may be a tumour antigen and may furthermore may be immunostimulatory or immunosuppressive or a combination thereof.

It is also envisaged that the methods of the invention allows for incorporation of one or more different antigens such that the exosomes may comprise e.g. an immunosuppressive antigen and an antigen against cytomegalovirus (CMV). Consequently, the exosomes according to the invention may comprise 1 or more antigens such as e.g. 2 or more different antigens, such as e.g. 3 or more different antigens, such as e.g. 4 or more different antigens, such as e.g. 5 or more different antigens, such as e.g. 6 or more different antigens of any kind or origin and may hence be a combination of one or more immunostimulatory antigens and one or more immunosuppressing agents.

Moreover, it is further contemplated that the exosomes according to the invention may be engineered to include any antigen (e.g. viral) to target a B-cell to be used as a vaccine (e.g. viral vaccine). It is also contemplated that the exosomes according to the invention may be used in the context of autoimmune diseases, allergy or in the context of treating subjects who/which have undergone transplantation of any kind and may risk having an immune response and thereby having the transplanted tissue rejected. This aspect can be realized by incorporating an immune suppressing agent in the exosome.

As indicated above, the excreted exosomes may be loaded with one or more antigens or one or more immunosuppressing agents or any combinations thereof by direct and/or indirect loading. However, the antigenic moiety may be chemically linked to the B. The chemical linking of the B-cell binding proteins or ligands can be realized by reacting the protein or ligand with a linker such as e.g. BS3 (Bis-(sulfosuccinimidyl)-suberate), DSS (Disuccinimidyl suberate), DSG (Disuccinimidyl glutarate) or the likes. As the linkers are bifunctional i.e. have two linking points, the protein or ligand coupled to the linker is then further reacted to couple the linker to the exosome to thereby have the protein or ligand coupled to the exosome via the linker molecule.

In the instance that immunosuppression is desired immunosppressive agents may be incorporated into the exosomes, such as e.g LMP-1, CTLA-4, PD1 or any mixtures thereof. However, it is to be clearly understood that any agent capable of acting as an immunosuppressant may be used according to the invention.

The details and particulars mentioned and discussed under the other aspects of the invention apply mutatis mutandis to the present aspect.

The B-cells may be transformed by e.g. Epstein-Barr virus (EBV) to thereby express the protein gp350. However, the transformation may also be performed by other techniques well known in the art to make the transformed B-cells express any protein capable of binding to a native B-cell receptor. Such receptor may be e.g. CD 19, CD21, CD 20, CD 23, CD79, BAFF-R, TACI, BCMA, IFN-R. Suitable ligands binding to such B-cell receptors may be e.g. BAFF, APRIL, gp350, EBV gp350/220 (gp350 (470t), CD23, C3b, iC3b, C3d, IFN-alpha, but any ligand capable of binding to a B-cell receptor may be used according to the invention. Consequently, the exosomes excreted from the B-cells may thus be engineered to express the same moieties capable of binding to a native B-cell as the transformed B-cell expresses. The inventors of present invention have surprisingly discovered that B-cell infected with EBV express gp350.

The culturing conditions of the transformed B-cells can be according to procedures well known in the art for expansion of cells.

For example, B cells may be cultured in a suitable medium such as e.g. MEM, DMEM or a complete RPMI 1640 medium (Invitrogen, Carlsbad, Calif.),. The medium may be supplemented with 10% exosome-depleted fetal calf serum, 100 IU/mL penicillin streptomycin, 2 mM L-glutamine, 50 µM β-mercaptoethanol and 25 ug gentamycin or any combinations thereof. If other cell types are used (other than B-cells) culturing of e.g. MDDCs or BMDCs growth factors may be added such as e.g. GM-CSF and IL-4 may be used in addition to the medium as stated above. The culturing is usually done during incubation at 37° C. in a humid incubator with 5% CO2 for 5 days, but may also be during $CO_2$-free conditions and during shorter periods of time such as e.g. about 2 days, such as e.g. about 3 days, such as e.g. about 4 days.

For culturing transformed B cells for harvesting supernatant for exosome preparation cells may be incubated for e.g. about 48 hr, such as about 72 hr, such as about 96 hr. For MDDCs or BMDCs culture, incubation is performed for e.g. 6 days to get immature DC then continue for another 48 hr to harvest the supernatant for exosome preparation. For antigen loading on BMDCs on day 6 the cells are pulsed/exposed with the antigen over night followed by washing and incubation for 48 hr at 37° C. in a humid incubator with 5% CO2 for 5 days.

It is to be understood that the above is a guiding instruction and may thus be varied within methods known in the art for culturing cells.

Specific examples are e.g. EBV-transformed B-cell lines may be cultured in complete medium consisting of RPMI-1640 (Gibco; Invitrogen Corp, Paisley, United Kingdom) supplemented with 25 µg/mL gentamicin (Gibco), 10% heat-inactivated Fetal Calf Serum (Hyclone, Logan, Utah), 2 mmol/L L-glutamine, 100 IU/mL penicillin (Gibco), 100 µg/mL streptomycin (Gibco), and 50 µmol/L β-mercaptoethanol (KEBO-lab, Spånga, Sweden). The medium was exosome-depleted. The cells may be cultured in a 37° C. humidified incubator with 6% CO2.

MDDCs culture peripheral blood mononuclear cells (PBMC) isolated by centrifugation on Ficoll Paque (Amersham Pharmacia Biotech AB, Uppsala, Sweden) according to the manufacturer's instructions. Cells may thereafter be washed in phosphate-buffered saline (PBS), resuspended in cell sorting buffer containing PBS, 0.5% bovine serum albumin (BSA) and 2 mm ethylenediaminetetraacetic acid (EDTA) and labelled with anti-CD14 magnetic beads (Miltenyi Biotech, Bergisch Gladbach, Germany) for positive selection of monocytes using automated matrix assisted cell sorting (AutoMACS; Miltenyi Biotech). CD14+ purity ranged between 82 and 99% (median 94%; n=29). Monocyte cell cultures were set up at a concentration of $4 \times 10^5$ cells/ml in culture flasks (Costar, Cambridge, UK) in complete culture medium containing RPMI 1640 (HyClone, Logan, Utah) with 10% exosome-depleted fetal calf serum (FCS; HyClone), 2 mm (l-glutamine (Gibco, Paisley, UK), 100 IU/ml penicillin (Gibco) with 100 µg/ml streptomycin (Gibco), 25 µg/ml gentamicin (Gibco) and 50 µm 2-(β-mercaptoethanol (Sigma Chemical Company, St Louis, Mo.) and 800 U/ml recombinant human (rh) IL-4 (BioSource International, Camarillo, Calif.) and 550 U/ml rhGM-CSF (BioSource International) with re-feeding on day 3. On day 6, cells were re-seeded in fresh medium with supplements and cell densities were adjusted to the same values for both conditions. The cell viability was determined on day 6 of culture by trypan blue exclusion. Culture supernatants were collected on day 8, centrifuged at 3000 g for 20 min at room temperature, and stored at −80°. Cells were harvested and phenotypes were analysed by flow cytometry on day 8.

For BMDCs culture: Bone marrow cells are cultured in complete RPMI 1640 medium (Invitrogen, Carlsbad, Calif.; 10% exosome-depleted fetal calf serum, 1 mM sodium pyruvate, 100 IU/mL penicillin streptomycin, 200 mM L-glutamine, 50 µM β-mercaptoethanol) in the presence of 10 ng/mL interleukin-4 (IL-4; Invitrogen) and 10% granulocyte macrophage colony-stimulating factor conditioned medium (Ag8653/X63 clone). At day 6, 50% of the culture supernatant is replaced with fresh medium. and the supernatant is harvested after 48 hr.

The cells may be cultured during a period of e.g. at least 2 day, such as e.g. at least 3 day, such as e.g. at least 4 days, such as e.g. at least 5 days, such as e.g. at least 6 days, such as e.g. at least 7 days, such as e.g. at least 2 weeks, such as e.g. at least 3 weeks, such as e.g. at least 1 month, such as e.g. at least 2 months, such as e.g. at least 3 months, such as e.g. at least 4 months, such as e.g. at least 5 months, such as e.g. at least 6 months.

The methods according to the invention enable a higher yield of exosomes which in turns allows for an effective treatment. The high yield is especially observed in EBV-transformed B-cells. The supernatant of the cell cultures may be harvested e.g. every two days, such as e.g. every $3^{rd}$ day, such as e.g. $4^{th}$ day, such as e.g. $5^{th}$ day such as e.g. every $6^{th}$ day, such as e.g. every $7^{th}$ day and may be harvested during any of the said intervals during a period of at least e.g. 1 month, such as e.g. at least 2 months, such as e.g. at least 3 months, such as e.g. at least 4 months, such as e.g. at least 5 months, such as e.g. at least 6 months.

The yield of exosomes using the methods according to the invention may be e.g. at least about 0.2 µg exosomes/1 million EBTB cells, such as e.g. at least about 0.3 µg exosomes/1 million EBTB cells, such as e.g. at least about 0.4 µg exosomes/1 million EBTB cells, such as e.g. at least about 0.5 µg exosomes/1 million EBTB cells, such as e.g. at least about 0.6 µg exosomes/1 million EBTB cells, such as e.g. at least about 0.7 µg exosomes/1 million EBTB cells, such as e.g. at least about 0.8 µg exosomes/1 million EBTB cells, such as e.g. at least about 0.9 µg exosomes/1 million EBTB cells, such as e.g. at least about 1.0 µg exosomes/1 million EBTB cells, such as e.g. at least about 1.5 µg exosomes/1 million EBTB cells, such as e.g. at least about 2.0 µg exosomes/1 million EBTB cells, such as e.g. at least about 2.5 µg exosomes/1 million EBTB cells, such as at least e.g. about 3.0 µg exosomes/1 million EBTB cells, such as e.g. at least about 5.0 µg exosomes/1 million EBTB cells or such as e.g. at least about 10.0 µg exosomes/1 million EBTB cells during a period of about e.g. 48 hours of culture of EBTB cells. The inventors of present invention have found that by EBV transformation of B-cells a higher yield of exosomes is observed, which usually is in the range of 0.1 µg exosomes/1 million cells when e.g. dendritic cells are used and cultured during the same period of time.

It is to be clearly understood that depending on the intended purpose or use of the exosomes, the suitable antigens are chosen; i.e. should the exosomes be intended for use in the context of treatment of e.g. cancer, one or more cancer antigens may be incorporated with the exosomes. Should the intended purpose of the exosomes be in the context of treatment of e.g. allergy one or more immunosuppressing agents may be incorporated with the exosomes to suppress the allergic reaction in question. This applies mutatis mutandis to the concept of e.g. transplantation. It is also to be clearly understood that it is also envisaged that one or more antigens may be combined with e.g. one or more further antigens or one or more immunosuppressing agents depending on the intended purpose or need.

The details and particulars mentioned and discussed under the other aspects of the invention apply mutatis mutandis to the present aspect.

Harvesting of the exosomes may be undertaken by e.g. ultracentrifugation or differential centrifugation or any combination thereof and subsequent collection of the pelleted exosomes. The pelleted exosomes may further be washes with a suitable medium such as e.g. PBS and optionally thereafter resuspended in a suitable medium whereafter the whole cycle of centrifugation, pelleting of the exosomes and washing with e.g. PBS, ay be repeated until an acceptable purity of the exosomes is reached.

It is to be clearly understood that present invention may be applied mutatis mutandis to other cell types such as e.g. dendritic cells or follicular dendritic cells (FDCs).

The details and particulars mentioned and discussed under the other aspects of the invention apply mutatis mutandis to the present aspect.

Method of Treatment

Present invention also relates to exosomes for use in the treatment of diseases, wherein the exosomes are targeting native B-cells, the method comprising
 (i) acquiring a biological sample from the subject such as e.g. a blood sample
 (ii) collecting B-cells from said sample in (i)
 (iii) transforming the collected B-cells in (ii) by suitable means such as e.g. a virus to thereby make said B-cell express a protein or ligand capable of binding to a native B-cell receptor.
 (iv) Culturing the transformed B-cells.
 (v) Collecting the excreted exosomes from the transformed B-cells in (iv)
 (vi) Transferring the exosomes in (v) back into the subject, and wherein the exosomes are directly and/or indirectly loaded with one or more antigens and/or immunosuppressing agents The sample collected from the subject in order to collect B-cells to be transformed, may be e.g. blood sample such as a peripheral blood or may be a bone marrow sample or a sample withdrawn from the lymphatic system of the subject or any combination or mixture thereof.

As indicated above, the exosomes may be loaded with one or more antigens by co-culturing the transformed B-cells (indirect loading) in (iv) with e.g. one or more antigens. On the other hand the method also allows for direct loading of the exosomes, i.e. after having harvested the exosomes in (v) the collected exosomes are subjected to e.g. one or more antigens before being transferred back into the patient. Direct loading is usually performed with fragments of proteins such as peptides or peptide fragments, such as e.g. peptide fragment comprising from 8 to 12 amino acid residues or from 15 to 24 amino acid residues. Alternatively, omitting indirect loading in (ii) necessitates loading in step (iv). Direct loading comprises contacting an EBTB exosome or a DC exosome with any antigen (one or more antigens of any kind independently of each other) under conditions promoting the uptake of the one or more antigens by the exosome. This may be e.g. under conditions comprising a shift in pH. This may be realized by suspending the exosomes in a suitable medium of a pH of at least pH 5, preferably about pH 5.2 at 4° C. Adding the peptide fragments and thereafter add a buffer such as e.g. TRIS-buffer to raise the pH to about pH 7.0 to thereby incorporate the peptide fragment to the exosome. There are also techniques for direct leading without the need to change the pH. However, it is also envisaged that multiple loading methods can be employed using both direct and indirect loading techniques.

The one or more antigens may be endogenous/autogenic (coming from the subject itself) or exogenous/allogenic (coming from another subject) or in the case of more antigens being incorporated into/onto the exosomes the antigens may be any mix of autogenic/allogenic antigens. Preferably the antigens are autogenic. Moreover, the one or more antigens may have any origin such as e.g. viral or bacterial or may be a tumour antigen and may furthermore may be immunostimulatory or immunosuppressive or a combination thereof.

It is also envisaged that the methods of the invention allows for incorporation of one or more different antigens such that the exosomes may comprise e.g. an immunosuppressive antigen and an antigen against cytomegalovirus (CMV). Consequently, the exosomes according to the invention may comprise 1 or more antigens such as e.g. 2 or more different antigens, such as e.g. 3 or more different antigens, such as e.g. 4 or more different antigens, such as e.g. 5 or more different antigens, such as e.g. 6 or more different antigens of any kind or origin and may hence be a combination of one or more immunostimulatory antigens and one or more immunosuppressing agents.

Moreover, it is further contemplated that the exosomes according to the invention may be engineered to include any antigen (e.g. viral) to target a B-cell to be used as a vaccine (e.g. viral vaccine). It is also contemplated that the exosomes according to the invention may be used in the context of autoimmune diseases, allergy or in the context of treating subjects who/which have undergone transplantation of any kind and may risk having an immune response and thereby having the transplanted tissue rejected. This aspect can be realized by incorporating an immune suppressing agent in the exosome.

As indicated above, the excreted exosomes may be loaded with one or more antigens or one or more immunosuppressing agents or any combinations thereof by direct and/or indirect loading. However, the antigenic moiety may be chemically linked to the B. The chemical linking of the B-cell binding proteins or ligands can be realized by reacting the protein or ligand with a linker such as e.g. BS3 (Bis-(sulfo-succinimidyl)-suberate), DSS (Disuccinimidyl suberate), DSG (Disuccinimidyl glutarate) or the likes. As the linkers are bifunctional i.e. have two linking points, the protein or ligand coupled to the linker is then further reacted to couple the linker to the exosome to thereby have the protein or ligand coupled to the exosome via the linker molecule.

In the instance that immunosuppression is desired immunosppressive agents may be incorporated into the exosomes, such as e.g LMP-1, CTLA-4, PD1 or any mixtures thereof. However, it is to be clearly understood that any agent capable of acting as an immunosuppressant may be used according to the invention.

The details and particulars mentioned and discussed under the other aspects of the invention apply mutatis mutandis to the present aspect.

The B-cells may be transformed by e.g. Epstein-Barr virus (EBV) to thereby express the protein gp350. However, the transformation may also be performed by other techniques well known in the art to make the transformed B-cells express any protein capable of binding to a native B-cell receptor. Such receptor may be e.g. CD 19, CD21, CD 20, CD 23, CD79, BAFF-R, TACI, BCMA, IFN-R. Suitable ligands binding to such B-cell receptors may be e.g. BAFF, APRIL, gp350, EBV gp350/220 (gp350 (470t), CD23, C3b, iC3b, C3d, IFN-alpha, but any ligand capable of binding to a B-cell receptor may be used according to the invention. Consequently, the exosomes excreted from the B-cells may thus be engineered to express the same moieties capable of binding to a native B-cell as the transformed B-cell expresses. The inventors of present invention have surprisingly discovered that B-cell infected with EBV express gp350.

The culturing conditions of the transformed B-cells can be according to procedures well known in the art for expansion of cells. The cells may be cultured during a period of e.g. at least 2 day, such as e.g. at least 3 day, such as e.g. at least 4 days, such as e.g. at least 5 days, such as e.g. at least 6 days, such as e.g. at least 7 days, such as e.g. at least 2 weeks, such as e.g. at least 3 weeks, such as e.g. at least 1 month, such as e.g. at least 2 months, such as e.g. at least 3 months, such as e.g. at least 4 months, such as e.g. at least 5 months, such as e.g. at least 6 months.

The methods according to the invention enable a higher yield of exosomes which in turns allows for an effective treatment. The high yield is especially observed in EBV-transformed B-cells. The supernatant of the cell cultures may be harvested e.g. every two days, such as e.g. every $3^{rd}$ day, such as e.g. $4^{th}$ day, such as e.g. $5^{th}$ day such as e.g. every $6^{th}$ day, such as e.g. every $7^{th}$ day and may be harvested during any of the said intervals during a period of at least e.g. 1 month, such as e.g. at least 2 months, such as e.g. at least 3 months, such as e.g. at least 4 months, such as e.g. at least 5 months, such as e.g. at least 6 months.

The yield of exosomes using the methods according to the invention may be e.g. at least about 0.2 µg exosomes/1 million EBTB cells, such as e.g. at least about 0.3 µg exosomes/1 million EBTB cells, such as e.g. at least about 0.4 µg exosomes/1 million EBTB cells, such as e.g. at least about 0.5 µg exosomes/1 million EBTB cells, such as e.g. at least about 0.6 µg exosomes/1 million EBTB cells, such as e.g. at least about 0.7 µg exosomes/1 million EBTB cells, such as e.g. at least about 0.8 µg exosomes/1 million EBTB cells, such as e.g. at least about 0.9 µg exosomes/1 million EBTB cells, such as e.g. at least about 1.0 µg exosomes/1 million EBTB cells, such as e.g. at least about 1.5 µg exosomes/1 million EBTB cells, such as e.g. at least about 2.0 µg exosomes/1 million EBTB cells, such as e.g. at least about 2.5 µg exosomes/1 million EBTB cells, such as at least e.g. about 3.0 µg exosomes/1 million EBTB cells, such as e.g. at least about 5.0 µg exosomes/1 million EBTB cells or such as e.g. at least about 10.0 µg exosomes/1 million EBTB cells during a period of about e.g. 48 hours of culture of EBTB cells. The inventors of present invention have found that by EBV transformation of B-cells a higher yield of exosomes is observed, which usually is in the range of 0.1 µg exosomes/1 million cells when e.g. dendritic cells are used and cultured during the same period of time.

The details and particulars mentioned and discussed under the other aspects of the invention apply mutatis mutandis to the present aspect.

Harvesting of the exosomes may be undertaken by e.g. ultracentrifugation or differential centrifugation or any combination thereof and subsequent collection of the pelleted exosomes. The pelleted exosomes may further be washes with a suitable medium such as e.g. PBS and optionally thereafter resuspended in a suitable medium whereafter the whole cycle of centrifugation, pelleting of the exosomes and washing with e.g. PBS ,ay be repeated until an acceptable purity of the exosomes is reached.

It is to be clearly understood that all aspects of present invention may be applied mutatis mutandis to other cell types such as e.g. dendritic cells or follicular dendritic cells (FDCs).

It is to be clearly understood that depending on the intended purpose or use of the exosomes, the suitable antigens are chosen; i.e. should the exosomes be intended for use in the context of treatment of e.g. cancer, one or more cancer antigens may be incorporated with the exosomes. Should the intended purpose of the exosomes be in the context of treatment of e.g. allergy one or more immunosuppressing agents may be incorporated with the exosomes to suppress the allergic reaction in question. This applies mutatis mutandis to the concept of e.g. transplantation. It is also to be clearly understood that it is also envisaged that one or more antigens may be combined with e.g. one or more further antigens or one or more immunosuppressing agents depending on the intended purpose or need.

The details and particulars mentioned and discussed under the other aspects of the invention apply mutatis mutandis to the present aspect.

The mode of administration of exosomes may be in various from known in the art such as e.g. parenteral administration and thus may be intravenous, intra-arterial, intraosseous intrathecal, intradermal or intraperitonal administration.

A sufficient dose of exosomes required for an effective immune response in a subject may be e.g. at least 0.1 mg/kg, such as e.g. at least 0.2 mg/kg, such as e.g. at least 0.3 mg/kg, such as e.g. at least 0.4 mg/kg, such as e.g. at least 0.5 mg/kg, such as e.g. at least 0.75 mg/kg, such as e.g. at least 0.9 mg/kg, such as e.g. at least 1.0 mg/kg, such as e.g. at least 3.0 mg/kg, such as e.g. at least 5.0 mg/kg, such as e.g. at least 7.0 mg/kg, such as e.g. at least 10.0 mg/kg, such as e.g. at least 15.0 mg/kg.

The exosomes can be administered as e.g. an intravenous infusion during a period of about 1 hour such as e.g. about 2 hours, such as e.g. 4 hours, such as e.g. 6 hours. Alternatively, the exosomes may also be administered as an injection in the time span of about 20 seconds such as about 30 seconds such as about 40 seconds, such as about 1 minute.

The treatment method according to the invention may be by administration of exosomes as a single dose or multiple doses. The treatment method may be performed once or repeated depending on the severity of the disease. Furthermore, the treatment may be reiterated upon recurrence of the disease.

The method of treatment is intended for cancer, allergy, autoimmune diseases and during therapy of transplantation. It is to be clearly understood that the treatment regimen may be combined or supplemented with other treatments such as e.g. in the context of cancer chemotherapy may be combined with the treatment according to the invention, or e.g. antihistamines may be combined in treatment of allergy, or e.g. antibiotics may be combined in treatment of infections etc with the method according to the invention.

The details and particulars mentioned and discussed under the other aspects of the invention apply mutatis mutandis to the present aspect.

Pharmaceutical Compositions

The exosomes may be formulated as a pharmaceutical composition suitable for e.g. parenteral administration to a subject such as, e.g., intravenous, intraarterial, intrathecal, intradermal, or intraperitonal administration.

When the exosomes are administered parenterally, they may be formulated in an isotonic medium, i.e. in a medium having the same tonicity as blood, and may further comprise one or more substances preventing aggregation of the exosomes. Saline solutions may be employed such as e.g. normal saline (NS) being a solution of about 0.91% w/v of NaCl, about 300 mOsm/L. However, other saline solutions may be used sun as e.g.:

Half-normal saline (0.45% NaCl), often with "D5" (5% dextrose), contains 77 mEq/L of Na and CI and 50 g/L glucose.

Quarter-normal saline (0.22% NaCl) has 39 mEq/L of Na and CI and always contains 5% dextrose for osmolality reasons.

Hypertonic saline may also be used such as e.g, concentrations greater than 2% NaCl administered via a central venous catheter. It is commonly available in two strengths:

3% NaCl has 513 mEq/L of Na and Cl.
5% NaCl has 856 mEq/L of Na and Cl.

The solutions may be further supplemented with Dextrose (glucose) such as e.g. Dextrose (glucose) 4% in 0.18% saline.

Further additives may be e.g. up to 3% human serum albumin such as, e.g. up to 2% human serum albumin or up to 1% human serum albumin.

For intravenously administration the concentration of exosomes in the composition to be administered normally lies within the range from about at least about 0.1 μg exosomes/ml medium, such as e.g. at least about 0.2 μg exosomes/ml medium, such as e.g. at least about 0.3 μg exosomes/ml medium, such as e.g. at least about 0.4 μg exosomes/ml medium, such as e.g. at least about 0.5 μg exosomes/ml medium, such as e.g. at least about 0.6 μg exosomes/ml medium, such as e.g. at least about 0.7 μg exosomes/ml medium, such as e.g. at least about 0.8 μg exosomes/ml medium, such as e.g. at least about 0.9 μg exosomes/ml medium, such as e.g. at least about 1.0 μg exosomes/ml medium, such as e.g. at least about 1.5 μg exosomes/ml medium, such as e.g. at least about 2.0 μg exosomes/ml medium, such as e.g. at least about 2.5 μg exosomes/ml medium, such as at least e.g. about 3.0 μg exosomes/ml medium, such as e.g. at least about 5.0 μg exosomes/ml medium or such as e.g. at least about 10.0 μg exosomes/ml medium or such as e.g. at least 15.0 μg exosomes/ml medium or such as e.g. at least 20.0 μg exosomes/ml medium.

The details and particulars mentioned and discussed under the other aspects of the invention apply mutatis mutandis to the present aspect.

Exosomes

Present invention also relates to exosomes, preferable exosomes originating from B-cells or from dendritic cells, follicular dendritic cells or the likes.

Exosomes according to the invention comprise at least one moiety or agent or protein or peptide fragment capable of binding to a receptor of a native B-cell. The receptors may be but are not limited to e.g. CD 19, CD21, CD 20, CD 23, CD79, BAFF-R, TACI, BCMA, IFN-R. Moreover, the one moiety or agent or protein or peptide fragment capable of binding to a receptor of a native B-cell may be but are not limited to e.g. BAFF, APRIL, gp350, EBV gp350/220 (gp350 (470t), CD23, C3b, iC3b, C3d, IFN-alpha. However, any lignad capable of binfing to a B-cell may be used according to the invention.

Furthermore, exosomes according to the invention may further comprise one or more antigens. The one or more antigens may be endogenous/autogenic (coming from the subject itself) or exogenous/allogenic (coming from another subject) or in the case of more antigens being incorporated into/onto the exosomes the antigens may be any mix of autogenic/allogenic antigens. Preferably the antigens are autogenic. Moreover, the one or more antigens may have any origin such as e.g. viral or bacterial or may be a tumour antigen and may furthermore may be immunostimulatory or immunosuppressive or a combination thereof.

The details and particulars mentioned and discussed under the other aspects of the invention apply mutatis mutandis to the present aspect.

It is also envisaged that the methods of the invention allows for incorporation of one or more different antigens such that the exosomes may comprise e.g. an immunosuppressive antigen and an antigen against cytomegalovirus (CMV). Consequently, the exosomes according to the invention may comprise 1 or more antigens such as e.g. 2 or more different antigens, such as e.g. 3 or more different antigens, such as e.g. 4 or more different antigens, such as e.g. 5 or more different antigens, such as e.g. 6 or more different antigens of any kind or origin and may hence be a combination of one or more immunostimulatory antigens and one or more immunosuppressing agents.

Moreover, it is further contemplated that the exosomes according to the invention may be engineered to include any antigen (e.g. viral) to target a B-cell to be used as a vaccine (e.g. viral vaccine). It is also contemplated that the exosomes according to the invention may be used in the context of autoimmune diseases, allergy or in the context of treating subjects who/which have undergone transplantation of any kind and may risk having an immune response and thereby having the transplanted tissue rejected. This aspect can be realized by incorporating an immune suppressing agent in the exosome. Such immunosuppressing agents may be but are not limited to e.g. LMP-1, CTLA-4, PD1 or any mixtures thereof. However, it is to be clearly understood that any agent capable of acting as an immunosuppressant may be used according to the invention.

The details and particulars mentioned and discussed under the other aspects of the invention apply mutatis mutandis to the present aspect.

Present invention also relates to exosomes (such as e.g. compositions thereof) for use in treatment of illness or condition in a subject. Illnesses or conditions may be e.g. cancer, any autoimmune disease, therapy under transplantation, allergies or any condition requiring immunosuppression or immunostimulation mutatis mutandis as to the description herein.

The present invention is based on the insight that exosomes (EBTB exosomes) released by Epstein-Barr virus-Transformed B cells (EBTB cells) target native B cells via CD21. The insight is supported by the finding that the interaction between EBTB cell exosomes and native B cells is efficiently blocked by anti-CD21, indicating an interaction between CD21 and the EBV glycoprotein gp350 or other ligands to CD21, e.g. CD 23, C3b, C3d or interferon-alpha. Other ligands that may be used according to the invention are e.g. BAFF, APRIL, EBV gp350/220 (gp350 (470t), CD23, C3b, iC3b, C3d, IFN-alpha. It is envisaged that any ligand or ligands capable of binding to a B cell receptor can be used according to the invention. The B-cell receptor may be, but is not limited to CD21 but may also be other receptors on native B-cells such as e.g. CD 19, CD21, CD 20, CD 23, CD79, BAFF-R, TACI, BCMA, IFN-R. Consequently, present invention can be seen as providing a ligand to the exterior of the exosomes capable of binding to a native B-cell and subsequent transfer of the one or more antigens incorporated into the exosome. This unexpected and surprising finding thus provides a more efficient transfer of the one or more antigens and thereby a more efficient and specific immune response.

Importantly, as the exosomes target B-cells and not T-cells a stronger T-cell response results than would be the case by direct stimulation of T-cells.

According to the present invention EBTB exosomes can be engineered in the laboratory to redirect their functional effects, such as by EBV transformation of B cells. The specific targeting of engineered EBTB exosomes towards native B cells potentiates their therapeutic usefulness. Furthermore, EBV transformation of B cells gives an unlimited source of exosomes.

According to the invention is thus disclosed an EBTB cell carrying a native B cell-targeting protein and a tumour antigen; the EBTB cell is capable of releasing EBTB exosomes carrying native B cell-targeting protein and tumour antigen.

According to the invention is also disclosed an EBTB exosome carrying a native B cell-targeting protein and a tumour antigen.

According to the invention is furthermore disclosed a dendritic cell (DC) exosome carrying a native B cell targeting protein and e.g. a tumour antigen or antigen from an infectious antigen (viral, bacterial or mycobacterial).

The exosomes of the invention may be loaded with and carry a single tumour antigen or a plurality of tumour antigens.

In this application the term "transformation" is intended to mean when (Epstein-Barr virus) EBV infects B-lymphocytes, and as a result thereof lymphoblastoid cell lines eventually emerge that are capable of indefinite growth. The growth transformation of these cell lines is the consequence of viral protein expression. The resulting cell line is sometimes referred to as an immortalised cell line.

In this application an "antigen" is intended to mean any substance able to elicit an immune response in a subject. To this end an antigen may be but is not limited to e.g. a viral antigen, bacterial antigen, mycobacterial antigen, tumour antigen or any substance that the subject's immune system responds to, e.g as encountered during transplantation or in an allergic reaction or during an autoimmune reaction.

In this application " tumour antigen" or "cancer antigen", which expressions comprise "tumour associated antigen", is a natural or synthetic peptide against which an organism to which it is administered forms antibodies or antigen-specific T cell responses. In particular, a tumour antigen is a natural or synthetic peptide capable of being presented by an antigen presenting cell (APC), in particular a B cell, an EBTB cell or an dendritic cell (DC). However, a tumour antigen of the invention can but need not be processed and presented by an antigen presenting cell to exert its antigenic effect.

The EBTB exosome or DC exosome of the invention may be loaded with a tumour antigen indirectly or directly. Indirect loading comprises culturing an EBTB cell or dendritic cell with tumour antigen under conditions promoting the uptake of the one or more antigens by the cell, and making the antigen-loaded cell release antigen-loaded exosomes. Direct loading comprises contacting an EBTB exosome or an DC exosome with tumour antigen under conditions promoting the uptake of tumour antigen by the exosome, in particular under conditions comprising a shift in pH.

According to the invention is furthermore disclosed the use of an EBTB cell and an EBTB exosome, and of a dendritic cell and a DC exosome of the invention in the treatment of cancer.

EBTB exosomes are capable of specifically targeting native B cells when provided with B cell-targeting proteins. Proteins particularly useful for such B cell-targeting are but not limited to gp350, CD23, C3b, CD19 and C3d.

According to the invention native B cells are isolated from blood taken from the circulation of a patient, transformed with EBV to EBTB cells, and cultured. The cultured EBTB cells are loaded with a cancer antigen. EBTB exosomes released from the cancer antigen-loaded EBTB cells are recovered. In this manner a number (amount) of EBTB exosomes loaded with cancer antigen sufficient for effective cancer treatment of the patient is generated. The EBTB exosomes of the invention loaded with a cancer antigen carry CD21 binding proteins.

Alternatively, native B cells isolated from blood taken from the circulation of a person other than the patient can be used, provided those B cells are immunologically compatible with the B cells of the patient to be treated. The method of the invention thus comprises the use of autologous and allogenic B cells.

It is preferred for the autologous/autogenic or allogenic antigen presenting native B cells of the invention and for EBTB cells obtained from them by infection with EBV to be expanded/proliferated in culture for a time period of at least two weeks such as e.g. at least 3 weeks, such as e.g. 4 weeks, such as e.g. 5 weeks, such as e.g. 6 weeks, such as e.g. 7 weeks, such as e.g. 8 weeks, such as at least 3 months, such as at least 4 months, such as e.g. at least 5 months, such as e.g. at least 6 month or more to provide a number of exosomes sufficient for the treatment of a patient. According to the invention agents involved in immune inhibition, such as LMP-1, comprised by EBTB exosomes may be neutralized prior to administration to the patient, such as by Fab-fragment molecules.

According to the invention is disclosed an exosome released by a CD40/IL-4-stimulated B cell ("CD40-stimulated B cell"). Long-term cultures of CD40-stimulated B cell lines are disclosed in M Wiesner et al. (2008), *Conditional Immortalization of Human B Cells by CD40 Ligation.* Plos ONE 3(1):e1464. Doi:10.1371/journal.pone.0001464. CD40-stimulated B cell lines and exosomes released from such B cells have a utility similar to that of the ETBT cell lines and ETBT exosomes. In particular, they may be loaded with tumour antigen and used in T cell and/or B cell activation.

The tumour antigen of the invention is an antigen presentable by a B cell, including an EBTB cell, or a dendritic cell, or by a corresponding endosome. In this application "tumour antigen" comprises an antigen expressed on the surface of a tumour cell, an antigenically active fragment thereof, in particular a tumour antigen peptide fragment comprising from 8 to 12 amino acid residues or from 15 to 24 amino acid residues capable of stimulating T cells. The term "tumour antigen" also comprises larger peptides or proteins capable of stimulating B cells without being presented on the surface of an antigen presenting cell. Such larger tumour antigen peptides or proteins can be advantageously employed in the invention in form of a tumour cell lysate, such as the one described in US 2007/0134275 A1.

According to the invention the tumour antigen of the invention is selected from the group consisting of: ERBB2 (HER2), BIRC5 (survivin), CEACAM5 (CEA), WDRK46 (BING4), BAGE (BAGE1), CSAG2 (TRAG-3), DCT (TRP-2), MAGED4, GAGE1, GAGE2, GAGE3, GAGE4, GAGE5, GAGE6, GAGE7, GAGE8, IL13RA2 (Interleukin 13 receptor alpha 2), MAGEA1, MAGEA2, MAGEA3, MAGEA4, MAGEA6, MAGEA9, MAGEA10, MAGEA12, MAGEB1, MAGEB2, MAGEC2, TP53, TYR (tyrosinase), TYRP1 (TRP-1), SAGE1 (SAGE), SYCP1 (HOM-TES-14/SCP1), SSX2 (HOM-MEL-40), SSX4, KRAS, PRAME, NRAS, ACTN4 (alpha-actinin-4), CTNNB1, CASP8 (caspase-8), CDC27, CDK4, EEF2, FN1 (fibronectin), HSPA1B (Hisp70), LPGAT1 (KIAA0205), ME1 (malic enzyme), HHAT (MART-2), TRAPPC1 (MUM-2), MUM3, MYO1B (unconventional myosin class 1 gene), PAPOLG (neo-PAP), OS9, PTPRK (receptor-like protein tyrosine phosphatase kappa), TPI1 (triosephosphate isomerase), ADFP (adiophilin), AFP (alpha-fetoprotein), AIM2, ANXA2 (annexin II), ART4 (endoplasmic reticulum-resident protein), CLCA2, CPSF1 (CPSF), PPIB (cyclophilin B), EPHA2, EPHA3, FGF5 (fibroblast frowth factor 5), CA9 (carbonic anhydrase 9), TERT (hTERT), MGAT5 (GNT-V; N-acetylglucosaminyltransferase V), CEL (intestinal carboxylesterase), F4.2, CAN (CAN-protein), ETV6 (TEL1), BIRC7 (livin/ML-IAP), CSF1 (macrophage colony stimulating factor), OGT, MUC1 (mucin), MUC2, MUM1, CTAG1A (NY-ESO-1; LAGE-2), CTAG2 (NY-ESO-ORF2; LAGE-1), CTAG (CAMEL), MRPL28 (melanoma antigen p15), FOLH1 (prostate-specific membrane antigen), RAGE, SFMBT1 (renal ubiquitous-protein 1), KAAG1 (RU2AS), SART1, TSPYL1 (SART-2), SART3, SOX10, TRG, WT1, TACSTD1 (Ep-CAM), SILV (Pmel17; gp100), SCGB2A2 (mammaglobin A), MC1R, MLANA (MART-1; Melan-A), GPR143 (OA1), OCA2 (P polypeptide), KLK3 (PSA; prostate-specific antigen), SUPT7L (ART-1), ARTC1, BRAF, CASP5 (caspase-5), uroplakin, CDKN2A, UBXD5(COA-1), EFTUD2 (elongation factor Tu GTP binding domain containing; nSNRP116), GPNMB, NFYC, PRDX5 (peroxiredoxin 5), ZUBR1 (RBAF600), SIRT2, SNRPD1, HERV-K-MEL, CXorf61 (KK-LC-1), CCDC110 (KM-HN-1), VENTXP1 (NA88A), prostate membrane specific antigen, SPA17 (sperm protein 17), KLK4, ANKRD30A (NY-BR1), RAB38 (NY-MEL-1), CCND1 (cyclin D1), CYP1B1 (P450 1B1), MDM2, MMP2 (matrix metalloproteinase-2), teratocarcinom-derived growth factor (CRIPTO-1), ZNF395 (PBF; papillomavirus biding factor), RNF43, SCRN1 (secernin 1), STEAP1 (STEAP), 707-AP, TGFBR2 (TGF-beta receptor type IIB), PXDNL (MG50), AKAP13 (lymphoid blast crisis oncogene (Lbc) oncoprotein), PRTN3 (proteinase 3), PSCA (prostate stem cell antigen), RHAMM (CD168), ACPP (prostatic acid phosphatase), ACRBP (OY-TES-1), LCK, RCVRN (recoverin), RPS2 (ribosomal protein S2), RPL10A (ribosomal protein L10a), SLC45A3 (prostein), BCL2L1 (BcI-xL),DKK1 (dickkopf-1), ENAH (human mena protein), CSPG4 (melanoma-associated chondroitin sulfate proteoglycan; MSCP), RGS5, BCR (breakpoint cluster region), BCR-ABL, ABL-BCR, DEK (DEK-oncogene), DEK-CAN, ETV6-AML1, LDLR-FUT, NPM1-ALK1, PML-RARA, SYT-SSX1, SYT-SSX2, FLT3 (FLT1), ABL1 (proto-oncogene tyrosine-protein kinase), AML1 (AML), LDLR (low density lipid receptor), FUT1 (GDP-L-fucose), NPM1 (NPM), ALK, PML1 (promyelocytic leukemia; PML), RARA (RARA alpha), SYT, SSX1, MSLN (mesothein), UBE2V1 (ubiquitin-conjugating enzyme variant Kua), HNRPL, WHSC2, EIF4EBP1, WNK2, OAS3, BCL-2, MCL1, CTSH (cathepsin H), ABCC3 (multidrug resistance-associated protein 3; MPR3), BST2 (HM1.24), MFGE8 (milk fat globule membrane protein BA46; lactadherin), TPBG (5T4 oncofetal antigen), FMOD (fibromodulin), XAGE1 (XAGE antigen), RPSA (oncofetal Ag immature laminin receptor; OFA-ILR), COTL1 (coactosin-like 1), CALR3 (CRT2), PA2G4 (ErbB3-binding protein 1), EZH2 (polycomb group protein enhancer of zeste homolog 2), FMNL1 (formin-related protein in leukocytes 1), HPSE (heparanase), APC, UBE2A, BCAP31, TOP2A, TOP2B, ITGB8, RPA1, ABI2, CCNI, CDC2, SEPT2, STAT1, LRP1, ADAM17, JUP, DDR1, ITPR2, HMOX1 (heme oxygenase-1; HO-1), TPM4 (tropomyosin-4), BAAT, DNAJC8, TAPBP, LGALS3BP (Mac-2-binding protein), PAGE4, PAK2 (P21-activated serin kinase 2), CDKN1A (cyclin-dependent kinase inhibitor 1A), PTHLH (parathyroid hormone-related protein; PTHrP), SOX2, SOX11, TRPM8 (prostate-specific protein transient receptor potential-p8), TYMS (thymidylate synthase), ATIC (5'-aminoimidazole-4-carboxamide-1-beta-d-ribonucleotide transfolmylase/inosinicase), PGK1 (phosphoglycerate kinase 1), SOX4, TOR3A (ATP-dependent interferon-responsive; ADIR), TRGC2 (T-cell receptor gamma alternate reading frame protein; TARP), BTBD2 (BTB domain containing 2), SLBP (harpin-binding protein), EGFR (epidermal growth factor receptor), IER3 (immediate early response gene X-1; IEX-1), TTK (TTK protein kinase), LY6K (lymphocyte antigen B complex locus K), IGF2BP3 (insulin—like growth factor (IGF)-II mRNA binding protein 3; IMP-3), GPC3 (glypican-3), SLC35A4, HSMD (HMSD-v-encoded mHA), H3F3A, ALDH1A1, MFI2, MMP14, SDCBP, PARP12, MET (c-Met protein), CCNB1 (cyclin B1), PAX3-FKHR, PAX3, FOXO1 (FKHR), ubiquilin-1, HOX-B6, IFI127, YB-1, KIAA0136, osteonectin, F-box only protein 21, ILF3, UBP3, BRAP-2; $H^+$-ATPase, KOO8-1, MAIAP, Gene AS, BR-1, BR-2, KIAA0603, TPR, NOR-90, N-CAM (neuronal cell adhesion molecule), Lewis Y carbohydrate antigen, Ep-CAM (epithelial cell adhesion molecule), MUC-1 protein, 36P6D5, sialyl Tn carbohydrate antigen, Globo H carbohydrate, CA 125, CA 19-9, CA 15-3, TAG-72, Her2/Neu receptor, p97, CD20, CD21, expression product of WT1 gene.

Further useful tumour-associated antigens are described, e.g, in DeVita et al., Eds, *Biological Therapy of Cancer*, 2nd Ed., Chapter 3: *Biology of Tumor Agents*. Lippincott Comp. 1995.

Squamous epithelial cell carcinoma antigens useful in the invention are disclosed in US 2007/0009501 A1.

Additional tumour-associated antigens are disclosed in U.S. Pat. Nos. 7,524,930, 7,427,660, 7,408,037, 7,432,354; 7,232,887; 7425607, 7,084239.

According to the invention is disclosed a polynucleotide encoding a tumour antigen peptide of the invention. It is preferred for the polynucleotide to be comprised by a polynucleotide capable of encoding a fused protein product from which the tumour antigen peptide is cleavable by a protease. The fused protein-encoding polynucleotide can be used for genetically modifying a native B cell, a dendritic cell or a EBTB cell of the invention to make the cell express the fused protein and transform it into the tumour antigen peptide of the invention. Thus genetically modified cells are capable of releasing exosomes carrying on their surface the tumour antigen peptide of the invention. However, there are also techniques for producing exosomes carrying the antigen in the cytosol.

According to the present invention is disclosed a method of treating cancer in a person by eliciting an immune response to an antigen displayed on cancerous cells of the patient, the method comprising:
  (a) providing a sample of peripheral blood from the person;
  (b) isolating B cells from the sample;
  (c) infecting the isolated B cells with Epstein Barr virus (EBV);
  (d) transforming the infected B cells to a latent stage but where gp350 is expressed;
  (e) culturing the EBV transformed B cells in the presence of cancer antigen;
  (f) harvesting exosomes released from the EBV transformed B cells;
  (g) administering the harvested exosomes to the patient to elicit said immune response.

Alternatively, instead of or in addition to culturing the EBV transformed B cells in the presence of cancer antigen, the method comprises contacting the harvested exosomes with cancer antigen to produce cancer antigen loaded exosomes.

According to the present invention is also disclosed a method of treating cancer in a person by eliciting an immune response to an antigen displayed on cancerous cells of the patient, the method comprising:
(a) providing a sample of peripheral blood from the person;
(b) isolating monocytes from the sample;
(c) culturing the monocytes to immature dendritic cells;
(d) modifying the immature dendritic cells to express a CD21-binding moiety;
(e) contacting the modified immature dendritic cells with a cancer antigen to transform them into cancer antigen loaded mature dendritic cells;
(f) harvesting cancer antigen loaded dendritic cell exosomes released from the mature dendritic cells;
(g) administering the cancer antigen loaded dendritic cell exosomes to the patient to elicit said immune response.

According to the present invention is furthermore disclosed a method of treating cancer in a person by eliciting an immune response to an antigen displayed on cancerous cells of the patient, the method comprising:
(a) providing a sample of peripheral blood from the person;
(b) isolating B cells from the sample; culturing the B cells;
(c) modifying the B cells to express a CD21-binding moiety;
(d) contacting the modified B cells expressing a CD21-binding moiety with a cancer antigen;
(e) harvesting cancer antigen loaded exosomes released from the cancer antigen-contacted modified B cells;
(f) administering the cancer antigen loaded B cell exosomes to the patient to elicit said immune response.

Alternatively, instead of or in addition to contacting the modified B cells with a cancer antigen, the method comprises contacting the harvested exosomes with cancer antigen to produce cancer antigen loaded exosomes.

In a method of treating cancer according to the invention, it is preferred for the CD21-binding protein moiety to comprise one or several of: gp350, EBV gp350/220 (gp350 (470t), CD23, C3b, iC3b, C3d, IFN-alpha.

According to the invention is furthermore disclosed: an exosome obtained or obtainable by the method of the invention; a method of producing the exosome; a cancer vaccine comprising the exosome; a T cell stimulated in vitro by the exosome; a B-cell or dendritic cell (DC) exosome comprising a CD21-binding moiety, in particular a CD21-binding moiety selected from the group consisting of: gp350, EBV gp350/220 (gp350 (470t), CD23, C3b, iC3b, C3d, IFN-alpha.

The invention is not limited to the treatment of a particular type of cancer. However, its application to the treatment of a cancer selected from group consisting of breast, bladder, skin, prostate, pancreas, ovary, thyroid, stomach, head and neck cancer, melanoma is preferred.

The invention will now be described in greater detail by reference to a number of preferred embodiments, some of which are illustrated in a number of figures.

DESCRIPTION OF THE FIGURES

FIG. 1 is a graph illustrating the attachment of EBV-transformed B cell exosomes (EBTB-exo) and of exosomes of a Burkitt's lymphoma cell line (BJAB) to native B cells, including blocking of interaction by anti-CD18 and anti-CD21, and by corresponding isotype control antibodies;

FIGS. 2a, 2b are graphs illustrating DC-exosome percentages (mean+s.d. for PBMC) of exosome-positive cells among peripheral blood mononuclear cells (PBMC) from three donors, measured as PKH67+ signal by flow cytometry at 1 h and 4 h;

Results are shown as % proliferating cells of total spleen cells.

Figure 11:
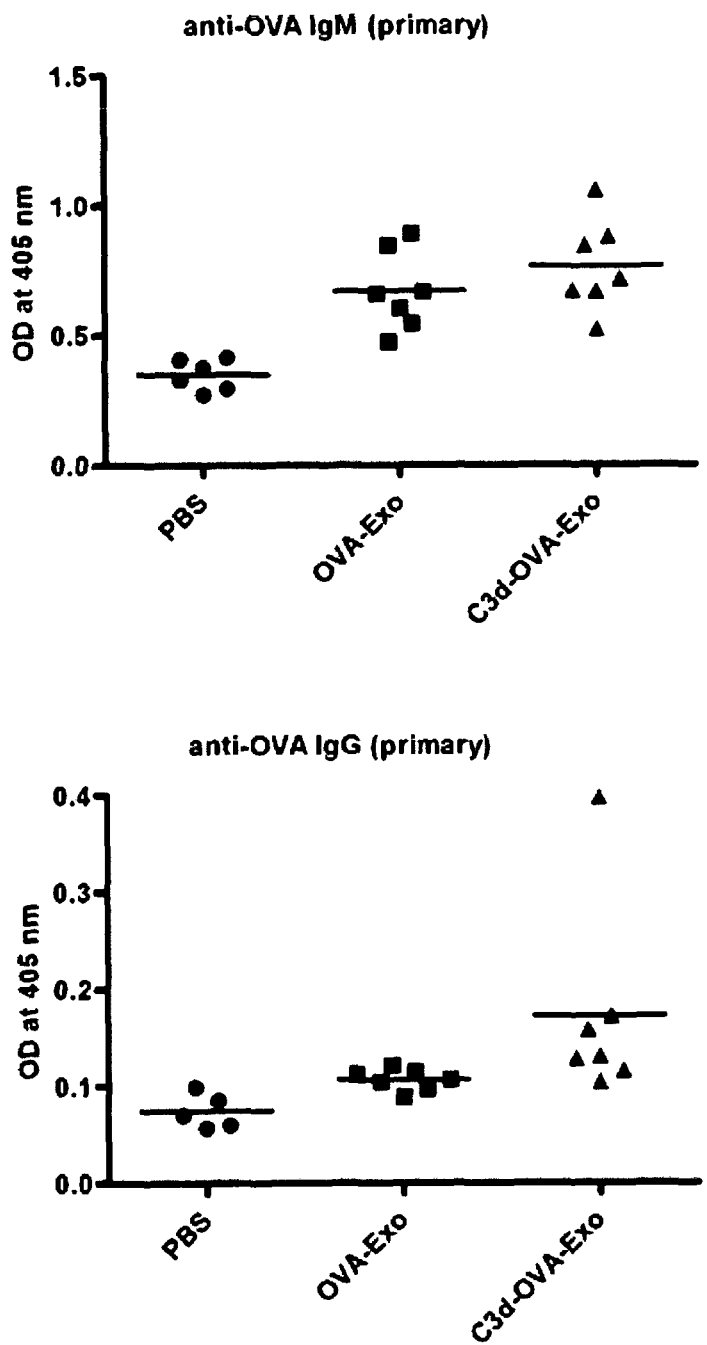

FIG. 11 Exosomes were prepared from the supernatant of the OVA pulsed Bone Marrow DC culture (OVAExo). For linking C3d on OVAExo the linker BS3 was mixed with C3d, followed by incubation for 30 min. Nonreacted reagent was removed by gel filtration and the elute containing C3d was added to the exosomes. The reaction was stabilized using glycine.

BALB/c mice were injected with 25 micrograms of OVAexo or C3dOVAExo and splenocytes were analysed in FACS after 3 days.

Figure 12:
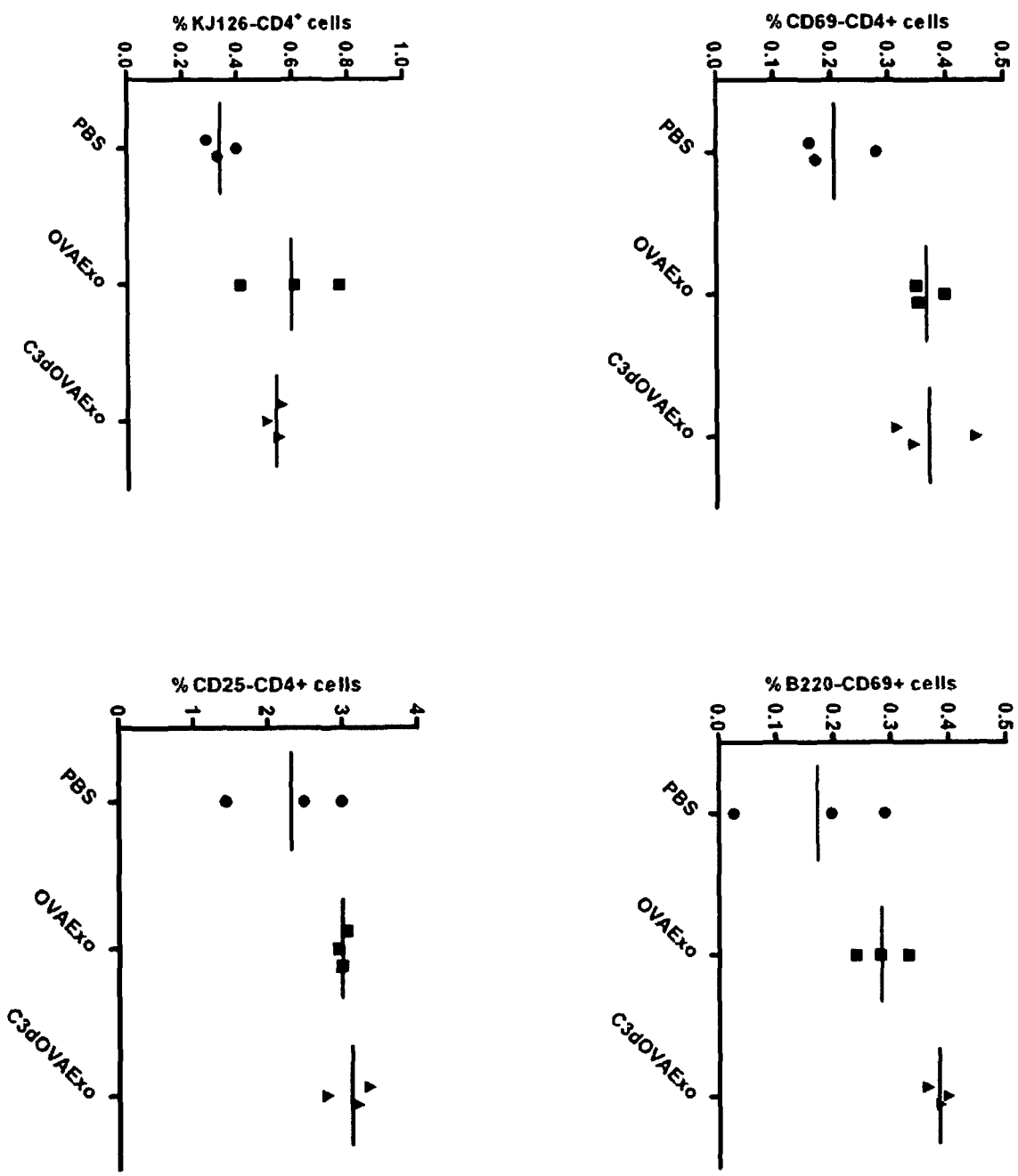

FIG. 12 inking C3d on OVAExo the linker BS3 was mixed with C3d, followed by incubation for 30 min. Nonreacted reagent was removed by gel filtration and the elute containing C3d was added to the exosomes. The reaction was stabilized using glycine.

DO11.10 OVA transgenic splenocytes were adoptively transferred to BALB/c mice followed by injection with 25 micrograms of OVAexo or C3dOVAExo the following day and splenocytes were analysed in FACS after 3 days.

Figure 13:
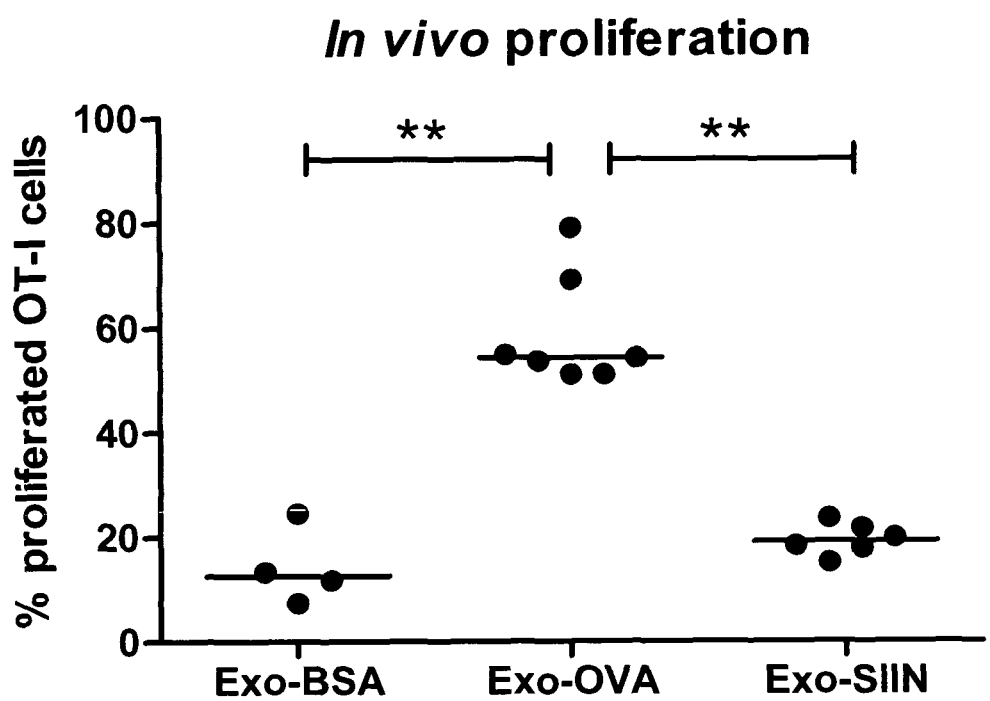

FIG. 13 CFSE labelled OT-I spleen cells were transferred to wild type C57BL/6 mice followed by injection with indirectly loaded exosomes with OVA (Exo-OVA), or directly loaded exosomes with the CD8 OVA peptide (Exo-SIIN) or a control (Exo-BSA) the following day. After 5 days spleen cells were analyzed for CFSE dilution by FACS for proliferation of OVA specific CD8+ cells.

Figure 14:
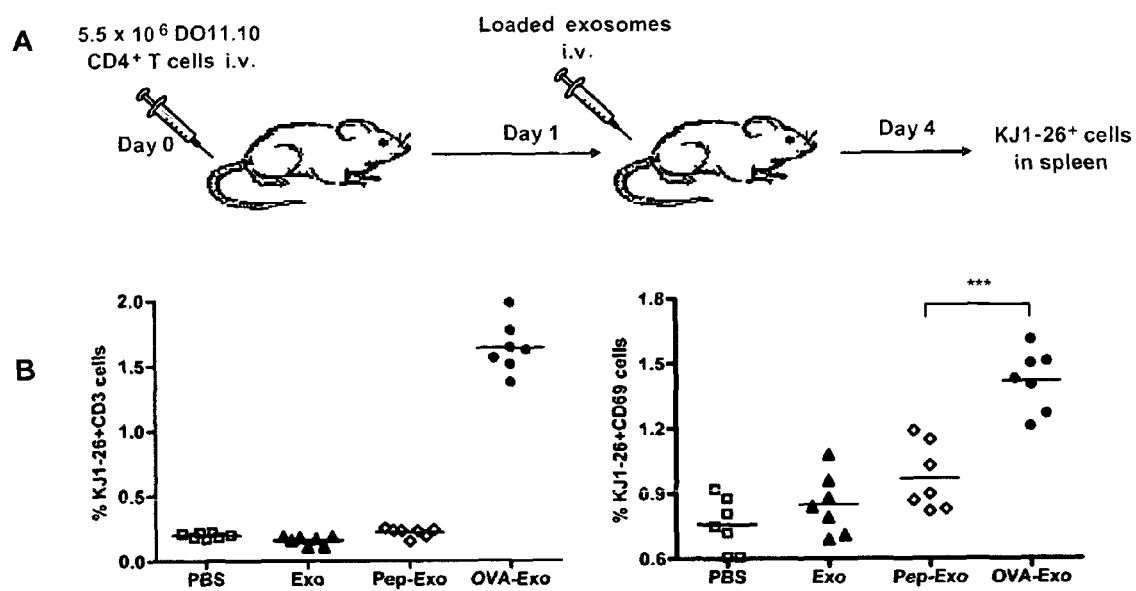

FIG. 14 FIG. 14A illustrates the immunization schedule in mice, wherein T-cells are injected into the mouse and one day thereafter exosomes are administered, whereupon 4 day after the immune response is measured. FIG. 14B shows the immune response by using directly loaded exosomes (Pep-Exo), indirectly loaded exosomes (OVA-exo), unloaded exosomes (Exo). PBS being the background. KJ1-26 is a monoclonal antibody specifically recognizing DO11.10tg TCR.

In the following experimental section illustrative examples are given as guidance. These examples are in no way to be construed as limiting.

EXPERIMENTAL SECTION

Interaction of Exosomes with Native B Cells and Peripheral Blood Mononuclear Cells Exosomes were isolated from culture supernatants of a human Epstein-Barr virus-transformed B cell line (EBTB cell line) and an EBV⁻ Burkitt's lymphoma cell line (BJAB cell line). The exosomes were compared with respect to their adherence to native B cells (FIGS. 1a, 1b) and to different cells in PBMC culture (FIGS. 2a, 2b). The exosomes were directly stained with a general membrane dye, PKH67 (Morelli A E et al., *Endocytosis, intracellular sorting, and processing of exosomes by dendritic cells*. Blood 2004, 104: 3257-3266. To see whether the exosomes retained their structure after staining with PKH67 they were bound to magnetic anti-MHC class II beads (Clayton, A et al., *Analysis of antigen presenting cell derived exosomes, based on immunomagnetic isolation and flow cytometry*. J Immunol Methods 2001, 247: 163-174). Flow cytometry analysis showed that green fluorescent MHC class II containing vesicles had been captured to the beads, and transmission electron microscopy (TEM) displayed nano-vesicles with intact lipid bi-layers, indicating that the PKH67 labeling did not interfere with exosome morphology. The different exosomes were then co-incubated with native B cells or human PBMC for 4 h and analyzed by multi-color flow cytometry. Treatment of the native B cells with anti-CD18 or anti-CD21 (20 µg/ml) preceded incubation with exosomes. Ten thousand cells were analyzed per sample.

The interaction between B cell exosomes and B cells is largely energy-independent and is therefore more likely mediated through adhesion molecules or surface receptors. EBTB exosomes express B cell receptors which, together with a distinct pattern of adhesion molecules, e.g. ICAM-1 and integrins (Clayton A et al., *Adhesion and signaling by B cell-derived exosomes: the role of integrins*. Faseb J 2004, 18:

977-979), might mediate the observed strong B cell preference of EBTB exosomes. However, the adhesion effect might alternatively or additionally be mediated by reminiscent EBV proteins or other proteins upregulated by the EBV-transformation expressed on the surface of EBTB exosomes.

Figure 3:
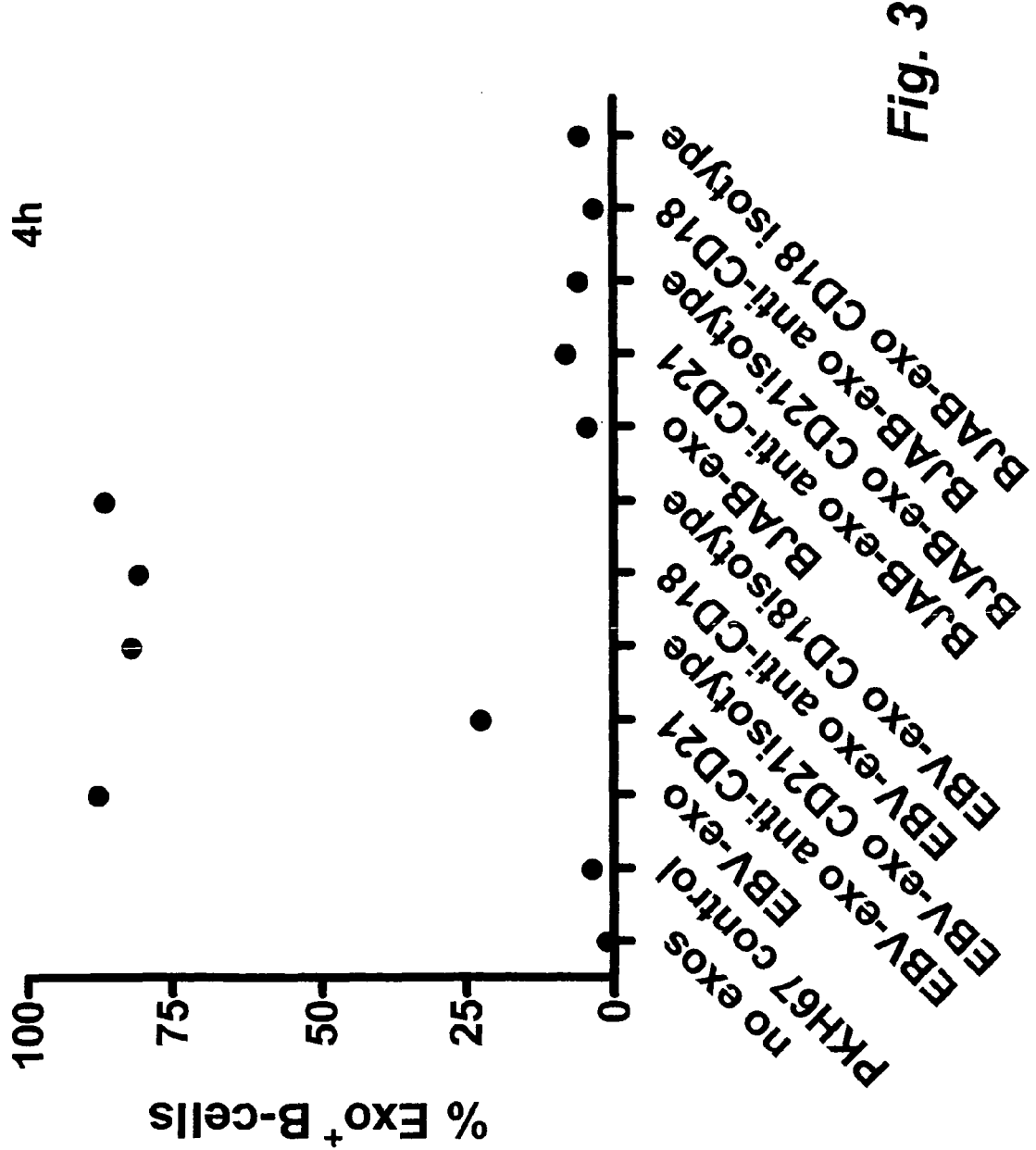
FIG. 3 is a graph illustrating EBV-exosome percentages (mean+s.d. for PBMC) of exosome-positive cells among peripheral blood mononuclear cells (PBMC) from three donors, measured as PKH67+ signal by flow cytometry at 4 h.

To investigate whether the B cell targeting of EBTB exosomes was similar to that of other B cell exosomes or specific for EBTB exosomes, the possible involvement of gp350, the B cell binding capacity of EBTB exosomes was compared with that of exosomes from an EBV⁻ Burkitt's lymphoma B cell line, BJAB27 (BJAB exosomes). It was found that BJAB exosomes did bind to a much lesser extent to native B-cells compared to EBTB exosomes, indicating the involvement of EBV in the binding (FIG. 3). To reveal the specificity of the binding, blocking of CD21 by anti-CD21 was attempted. It was found that anti-CD 21 efficiently blocked the interaction between EBTB exosomes and native B cells. This suggests that the binding between B cells and EBTB exosomes is caused by an interaction between the receptor CD21 on native B cells and a ligand on EBTB exosomes, possibly gp350 or CD23. To rule out additional involvement of integrins as LFA-1 (CD11a/CD18), Mac-1 (CD11b/CD18) and p150,95 (CD11c/CD18) in the binding, these integrins were blocked by anti-CD18. As evident from FIG. 3, this blocking does however not affect the interaction between EBTB exosomes and native B cells. CD21 thus seems obligatory for B cell/B cell exosome binding.

The possibility of EBV particles residing in the EBTB cell line, and thus the risk that they could contaminate the exosome preparations, was ruled out by ascertaining that the B cell bound PKH67 stained vesicles were exosomes indeed, not EBV particles. Exosome preparations from EBV⁺ B cells and samples from exosome and B cell co-cultures were carefully checked by TEM. Virus particles could neither be detected among the exosomes nor on the B cells (data not shown).

While it is known that different cell types produce exosomes with phenotypes that reflect their cells of origin, the question of how exosomes from different cell types differ in their targeting of cells remained to be elucidated. It was found that, independently of origin, such native exosomes seem to have the same main target in human peripheral blood, i.e. HLA⁻DR⁺CD14⁺ cells, by which they appear to be actively phagocytised. However, EBTB exosomes were found to produce exosomes that had their specificity changed from HLA-DR⁺CD14⁺ cells towards native B cells. This was demonstrated by comparing exosomes from the BJAB cell line (BJAB exosomes), an EBV⁻ B cell line, with exosomes from the EBTB cell line (EBTB exosomes), an EBV⁺ B cell line. The high interaction between EBTB exosomes and native B cells could be efficiently blocked by anti-CD21 but not by anti-CD18. This novel mechanism of targeted B cell intercommunication may also reflect the situation in vivo in EBV infected individuals. It might have an important role in long-term immune protection against EBV.

Methods

Exosome Sources. Buffy coats from healthy blood donors at the blood bank of Karolinska University Hospital were used for Ficoll Paque (Amersham Pharmacia Biotech AB, Uppsala, Sweden) separation of peripheral blood mononuclear cells (PBMCs). The Epstein Barr Virus (EBV) transformed B cell line was a kind gift from Dr. Barbara Bohle, Medical University of Vienna, Vienna, Austria. The EBV-negative lymphoma B cell line, BJAB, was a kind gift from Michael Karlsson, Karolinska Institutet.

Exosome Isolation. Exosomes were isolated from cell culture supernatants (B cell lines) using differential centrifugations starting at 300×g for 10 min to remove cells followed by 3,000×g for 20 min and then ultra centrifuged (Ti45 rotor in Optima L-100 XP Ultra centrifuge, Beckman Coulter, Fullerton, Calif., USA) at 10,000×g for 30 min at 4° C. to deplete supernatants of possible cell debris. Ultra centrifugation at 100,000×g for 70 min pelleted the exosomes that were subsequently washed in PBS repeating the last ultra centrifugation. The pelleted exosomes were re-suspended immediately after the last wash in a small volume of PBS and protein concentrations were determined using the BioRad Dc assay (BioRad, Hercules, Calif., USA) according to the manufacturer's protocol. The same amount of protein from each of the four exosomes sources was used.

Co-Incubation of Peripheral Blood Mononuclear Cells with Exosomes. Buffy coats from healthy blood donors were used as a source of freshly isolated PBMCs. Cells were isolated on Ficoll Hypaque (Amersham Pharmacia Biotech AB) according to the manufacturer's instructions. Remaining red blood cells were lysed using ACK lysis buffer for 5 min (0.15 M $NH_4Cl$, 10 mM $KHCO_3$, 0.1 mM $Na_2EDTA$, pH 7.2). PBMCs were incubated in CCM with PKH67⁺ exosomes at 10 µg/5×10⁵ cells in 6 ml tubes at 37° C. for 4 h. Some experiments were performed at 4° C.

Exosome Staining. Exosomes were stained using the green fluorescent dye PKH67 (Sigma Aldrich, Saint Louis, Mo., USA) for general membrane labeling. Exosomes were transferred from PBS to dilutent C (Sigma) solution by centrifugation at 100,000×g for (NVT90 rotor, Beckman Coulter) for 70 min. PKH67 stain was diluted to 4 µM 2× stock in the same volume as the exosome sample (300 µg/mL in diluent C), the stock was filtered in a small 0.2 µm syringe filter to remove potential aggregates formed by the stain. The exosome sample was then passed through a 0.2 nm syringe filter when mixed with the PKH67 stock solution 1:1 and allowed to stain for 5 min at RT before stopping with 1% BSA for 1 min. The exosomes were then washed with CCM and centrifuged in the NVT90 rotor as described above. Pellets were rinsed carefully to remove unbound PKH67 stain. Preliminary microscopic analysis showed that exosomes formed aggregates after staining (data not shown), and were thus re-suspended in CCM and filtered through a small volume 0.2 µm syringe filter immediately before addition to cells. As a control the same concentration of PKH67 was centrifuged in parallel to create a background control for potentially pelleted unbound stain.

Co-Culture of PKH67 Stained Exosomes with PBMC. Pre-filtered PKH67 stained exosomes were added to PBMC for 1 and 4 h at 37° C., as well as 4° C. during temperature studies. 10 µg of exosomes per 5×105 PBMC were added. As a background control the PKH67 dye pellet centrifuged in parallel was used.

Transmission Electron Microscopy (TEM). Exosomes were captured on anti-HLA class II magnetic beads (Clayton, A et al., *Analysis of antigen presenting cell derived exosomes, based on immuno-magnetic isolation and flow cytometry.* J Immunol Methods 2001, 247: 163-174). The beads were fixed in 2% glutaraldehyde in 0.1 M sodium cacodylate buffer containing 0.1 M sucrose and 3 mM $CaCl_2$, pH 7.4 at 4° C. over night, and centrifuged to a pellet. The pellet was rinsed in 0.15 M sodium cacodylate buffer containing 3 mM $CaCl_2$, pH 7.4 followed by post-fixation in 2% osmium tetroxide in 0.07 M sodium cacodylate buffer containing 1.5 mM $CaCl_2$, pH 7.4 at 4° C. for 2 h, dehydrated in ethanol followed by acetone and embedded in LX-112 (Ladd, Burlington, Vt., USA). Sections were contrasted with uranyl acetate followed by lead citrate and examined in a Tecnai 10 transmission electron microscope (Fei, Acht, The Netherlands) at 80 kV. Digital images were captured by a MegaView III digital camera (Soft Imaging System, GmbH, Münster, Germany).

Flow Cytometry. PBMCs were stained using two different mouse monoclonal (m)Ab panels: "APC" anti-HLA-DR (MHC class II) PECy5, anti-CD14-PE, and anti-CD19 Pacific Blue (or PE-Texas Red), and "T cells" anti-CD8 APC (or PECy5), anti-CD4 PE, and CD3 Pacific Blue (BD Biosciences, San Jose, Calif., USA). Gating was first done on lymphocyte/monocytes in FSC/SSC. For the panel APC, HLA$^-$DR$^+$CD14$^+$ and HLA$^-$DR$^+$CD14$^-$ populations were first gated. Then out of HLA$^-$DR$^+$CD14$^-$ cells the CD19$^+$ cells were gated. For the T cell panel, the populations were selected as CD3$^+$CD4$^+$ versus CD3$^+$CD8$^+$ directly out of the lymphocyte/monocyte gate. For each subpopulation the corresponding PKH67$^+$ gates were set on the sample without exosomes. The samples were run on a FACS Aria flow cytometer (BD Biosciences). Compensation controls of single stained cells were done before data collection from each individual and compensations were calculated automatically by the FACS Diva (BD Biosciences) software used for analyses of acquired data. In the lymphocyte/monocyte gate 10,000 events per sample were collected.

Confocal Laser-Scanning Microscopy (CLSM). Following incubation for 4 h with PKH67+ exosomes at 4° C. or 37° C., PBMC were fixed in 4% formaldehyde for 15 min. Staining was carried out using either anti-CD3, anti-CD14 or anti-CD19 mAb (BD Biosciences) according to the manufacturer's instructions, followed by washing with PBS. A secondary goat anti-mouse mAb labeled with Alexa Fluor 546 (Molecular Probes, Eugene, Oreg., USA) was used for detection. After cytospin, slides were mounted with 90% glycerol. Florescent images were acquired on a CLSM (TCS SP2; Leica Microsystems, Mannheim, Germany) equipped with one argon and two HeNe lasers. PKH67 was excited with a 488-nm laser line detecting light in the wavelength region of 490-530 nm. Alexa 546 was excited by a 543-nm laser line with detection of light in the region of 580-700 nm.

Image Stream Analysis. Exosomes were stained and co-incubated with PBMC as described for flow cytometry. Cells were run on the ImageStream® multispectral imaging flow cytometer and images were analyzed using IDEAS® image analysis software (Amnis Corporation, Seattle, Wash., USA). 10 000 events were collected in each sample and single stained compensation controls were used to compensate fluorescence between channel images on a pixel by pixel basis. Gating was done according to the principle for FACS. The cellular location of the PKH67 fluorescence, was measured using the Internalization feature. The Internalization feature is defined as a ratio of the intensity inside the cell to the intensity of the entire cell. The higher the score, the greater the concentration of intensity inside the cell. The inside of the cell is defined by an erosion of a mask that fits the membrane of the cell. The feature is invariant to cell size and can accommodate concentrated bright regions and small dim spots. The ratio is mapped to a log scale to increase the dynamic range to values between $\{-inf, inf\}$. Cells with primarily internal fluorescence have positive scores while cells showing little internalization have negative scores.

Blocking Assays. PBMC (106/ml) were either co-incubated with mAbs to CD18 (clone MEM48), CD21 (clone B-E5) or isotype-matched Abs (20 µg/ml; Nordic BioSite, Täby, Sweden) for 30 min in cell culture media at RT, and thereafter washed with PBS before exosomes were added at 10 µg/5×105 cells at 37° C. for 1 or 4 h. FACS analysis was performed as previously described. LCL1-exosomes were treated with anti-CD23 (clone 9P25, 30 µg/ml Beckman Coulter) or with the supernatant (30% of total volume) from a mouse hybridoma culture producing the gp350/250 neutralizing mAb 72A1 (DSMZ, Braunschweig, Germany). An irrelevant isotype control or hybridoma supernatant were used as controls. After 30 min in cell culture media at RT, pre-treated LCL1-exosomes were added to B cells (10 µg/2.5×105 cells) for 4 h, before performing FACS analysis. The B cells had been isolated from PBMC using B cell isolation kit II (Miltenyi Biotech).

Intracellular Flow Cytometry Staining. LCL1- and BJAB cells (5×104) were fixed with 4% formaldehyde for 5 min at RT. After three washing steps with PBS, cells were incubated for 10 min in 1% saponin solution at RT. Cells were stained with the primary mAb 72A1 against gp350/250 by adding the supernatant from the mouse hybridoma culture at RT for 1 h. After two washing steps with 0.1% saponin solution, cells were incubated with the secondary Alexa Fluor 488 (Invitrogen, Calif., USA) Ab for 45 min at RT, washed and analyzed by flow cytometry.

Sucrose Gradient. Fractions of exosome preparations were collected by sucrose gradient as previously described (5). These were directly loaded onto anti-MHC class II Dynabeads (Dynal, Oslo, Norway) for flow cytometry analysis or pelleted by centrifugation at 200 000×g for 35 min at 4° C. for immunoblot analysis.

Immunoblot Analysis. Each pelleted exosome fraction was separated by SDS-PAGE (12%) and transferred to polyvenylidene difluoride membranes (Millipore, Mass., USA). Membranes were stained with mAbs to LMP1 (clone CS. 1.4; DakoCytomation), gp350 (clone 2L10, Millipore, Mass., USA), CD81 (clone H-121, Santa Cruz Biotechnology, Calif., USA) or HLA-DR (clone TAL.1B5, DakoCytomation, Glostrup, Denmark) according to the manufacturer's instructions. Membranes were visualized with ECL Advance Western Blotting Detection kit and exposed on Hyperfilms (GE Healthcare, Uppsala, Sweden).

Cord Blood Transformation Assay. Heparinized cord blood samples, obtained from the Karolinska University Hospital and approved by the local ethics committee, were subjected to Ficoll Paque density centrifugation. One million cord blood mononuclear cells (CBMCs) were either incubated with the 10 000×g pellet from BJAB or LCL1 supernatants or with 24 µg of the BJAB or LCL1 exosome preparations for 1.5 h in a humidified 37° C., 5% CO2 incubator. CBMCs were washed and resuspended in complete RPMI at 106 cells/mL and seeded in quintuple at 2×105 cells per well/200 µL, in 96-well plates. As a positive control for EBV induced cell transformation, CBMC were exposed to B95-8 virus containing supernatant. Culture medium served as negative control. CBMCs were fed weekly with fresh medium. On the 33rd day, the transformation was registered visually by the appearance of typical cell aggregates and by thymidine incorporation assay. One µCi 3H-thymidine (GE Healthcare) was added to the cultures and incubated for 16 h. CBMCs were harvested onto glass fiber filters and radioactivity was measured in a scintillation counter (1205 Betaplate, Wallac).

NanoSight. Size distribution within exosome preparations were analyzed by measuring the rate of Brownian motion using a NanoSight® LM10 system which is equipped with a fast video capture and a particle tracking software (NanoSight Ltd., Amesbury, UK). EBV (strain B95-8), used as a control, was a kind gift from Dr. Kerstin Falk (Department of Microbiology, Tumour and Cell Biology, Karolinska Institutet). Prior analysis with NanoSight, EBV was heat inactivated for 20 min at 56° C.

Statistical Analyses. Wilcoxon matched pairs test was used to compare differences between groups using the GraphPad Prism software version 4.03. P-values below 0.05 were considered significant.

Generation of an EBV Infected B Cell Line. A mononuclear cell suspension comprising B cells was isolated from peripheral blood (50 ml) obtained from a melanoma cancer patient selected for treatment or from an immunologically compatible donor by the method of the invention. An EBV infected B cell line (EBTB cell line) was prepared from this suspension by following the protocol devised by Tosato and Cohen (Curr Protoc Immunol 2007, 7.22.1-7.22.4).

Isolation of EBTB Exosomes. EBTB exosomes were isolated from the EBTB cell line essentially as described above for exosomes from native B cells.

EBTB Exosome Loading. The isolated EBTB exosomes were loaded with MHC class I and II peptides or cancer antigen peptides by adapting the methods of N Chaput et al. (Exosomes as potent cell-free peptide-based vaccine. II. *Exosomes in CpG adjuvants efficiently prime native Tcl lymphocytes leading to tumor rejection.* J immunol 2004, 172:2137-2146) and D H Hsu et al. (*Exosomes as a tumor vaccine enhancing potency through direct loading of antigenic peptides.* J Immunol 2003, 26:2137-2364).

Purification of Antigen-Loaded ETBT Exosomes. The antigen-loaded EBTB exosomes were purified by the method of B. Escudier et al. (*Vaccination of metastatic melanoma patients with autologous dendritic (DC) derived-exosomes: results of the first phase I clinical trial.* J Translat Med 2005, 3:10).

In-Vitro CD-40/IL-4 Stimulated B Cell Line Exosomes. Buffy coats from a healthy blood donor at the blood bank of Karolinska University Hospital was used for Ficoll Paque (Amersham Pharmacia Biotech AB, Uppsala, Sweden) separation of peripheral blood mononuclear cells (PBMCs). Three parallel cultures of about $1\cdot10^5$ PBMC each were established and stimulated by following the protocol of Wiesner et al., supra. Two of the cell lines were maintained for 70 days whereas the third cell line ceased to proliferate after about three weeks. The two long-term CD40-stimulated B cell lines were found to be free of EBV infected lymphoblasts and other cell types. Exosomes were isolated from the supernatant of one of the two cell cultures in the same manner as described above for ETBT exosomes.

The isolated exosomes were loaded with tumour antigen and purified as described above for ETBT exosomes.

Results

Exosomes Derived from Human DC and Breast Milk Target Monocytes, While LCL1 Exosomes Prefer B Cells In order to elucidate the binding of different exosomes to immune cells we compared exosomes isolated from human monocyte derived DC, an EBV transformed lymphoblastoid B cell line (LCL1), and from human breast milk with respect to their adherence to PBMC. Exosomes were stained with a green fluorescent membrane dye, PKH67, to be detectable by flow cytometry. To see whether exosomes were properly labeled and that their structures were retained after staining with PKH67, the exosomes were bound to magnetic anti-MHC class II bead. Flow cytometry analysis showed that green fluorescent MHC class II containing vesicles had been captured to the beads and TEM displayed nano-vesicles with intact lipid bi-layers, indicating that the PKH67 labeling did not interfere with exosome morphology. The different exosomes were then co-incubated with PBMC for 1 or 4 h and analyzed by multi-color flow cytometry to evaluate the association pattern of exosomes to cells. After 1 h DC-derived exosomes mainly interacted with monocytes (HLA-DR$^+$CD14$^+$; average 46%), whereas only 17% bound to B cells (HLA-DR$^+$CD14$^-$CD19$^+$; FIG. 4A). In contrast, LCL1 exosomes showed a reverse pattern of association with a strong preference for B cells. 63% of the B cells were positive for LCL1 exosomes whereas on average only 17% of the monocytes had associated with these exosomes at 1 h (FIG. 4B). After 4 h of co-incubation there was a general increase in percentages of exosome positive cells within each cell population, but the distinct association patterns to the different cell populations remained (FIG. 4D-F). Milk exosome interactions were generally low after 1 h of co-incubation (FIG. 4C). However, at 4 h 55% of the monocytes and 18% of the B cells had associated with milk exosomes (FIG. 4C), resembling the pattern for DC exosomes at 1 h. Previously we have found that milk exosome preparations have a lower content of exosomal vesicles in relation to the total protein amount in the exosome pellet compared to pellets from other exosome types. Accordingly, when increasing the amount of milk exosomes 5 times (50 µg/5×10$^5$ PBMC), the level of milk exosome interaction at 1 h reached an average of 64% with monocytes and 26% with B cells (n=3, data not shown). These are comparable levels as seen at 1 h when incubating with DC exosomes at 10 µg/5×10$^5$ PBMC, suggesting higher amounts of non-exosomal proteins in the milk exosome preparations compared to the other exosome preparations.

Figure 4:
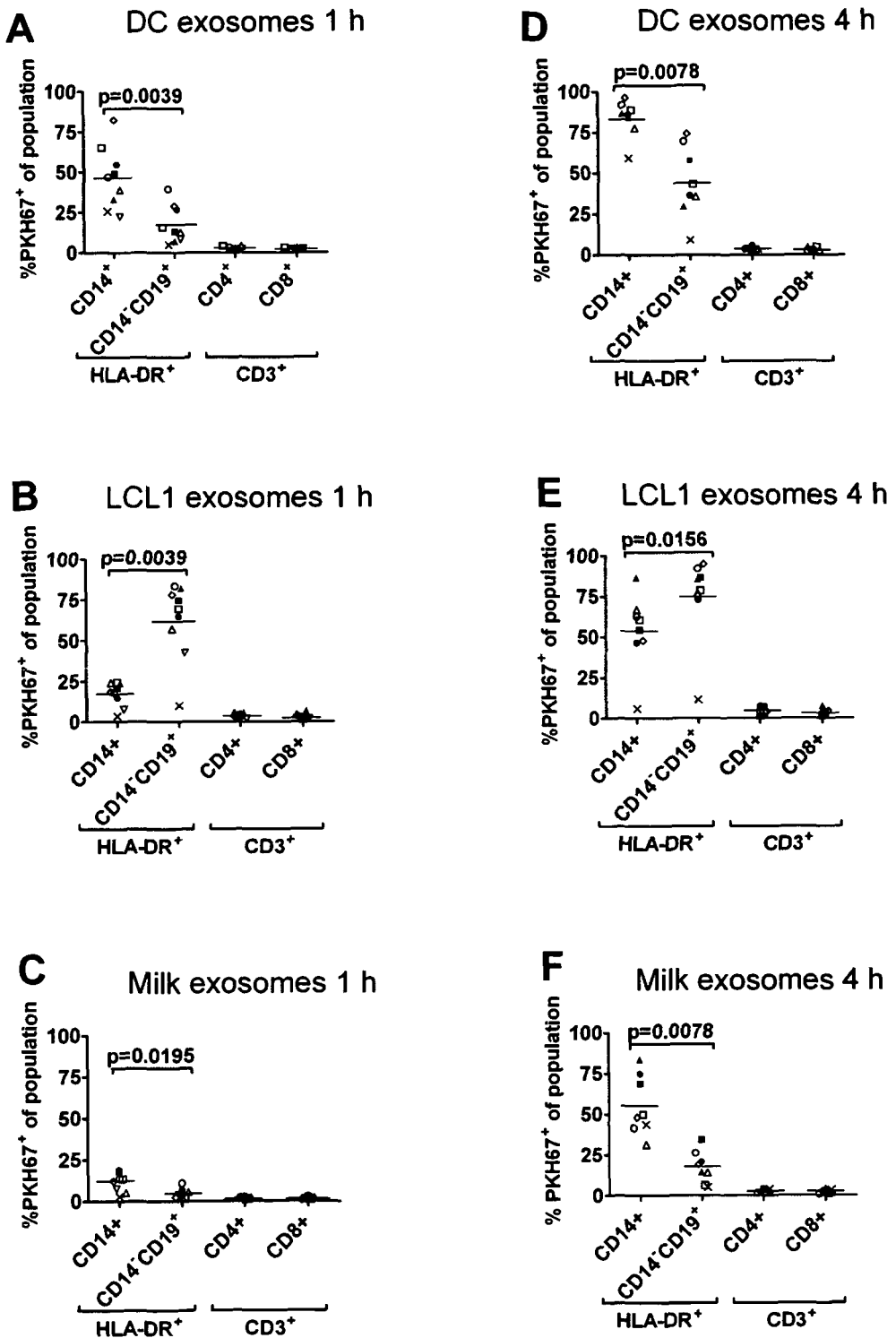
FIG. 4 Exosomes target specific subpopulations in PBMC. PKH67 stained (A, D) DC-, (B, E) LCL1- and (C, F) breast milk-exosomes, were incubated with PBMC from healthy blood donors for 1 h (A-C, n=9) and 4 h (D-F, n=8). 10 µg of exosomes per 5×105 PBMC were added. As a background control the PKH67 dye pellet centrifuged in parallel was used, which showed low to undetectable fluorescence (data not shown). Association of exosomes was measured by collection of 104 events per sample in four-color flow cytometry. Data are expressed as percent PKH67+ cells out of cells in each subpopulation. Bars indicate mean values. Different blood donors are indicated by individual symbols.

Although T cells constitute the majority of the PBMC (in our study around 70%), less than 8% of either CD4$^+$ or CD8$^+$ T cells showed associations with any of the exosomes after 4 h (FIG. 4). No consistent differences in preferences for CD4$^+$ compared to CD8$^+$ T cells with the different exosome types were observed.

Figure 5:
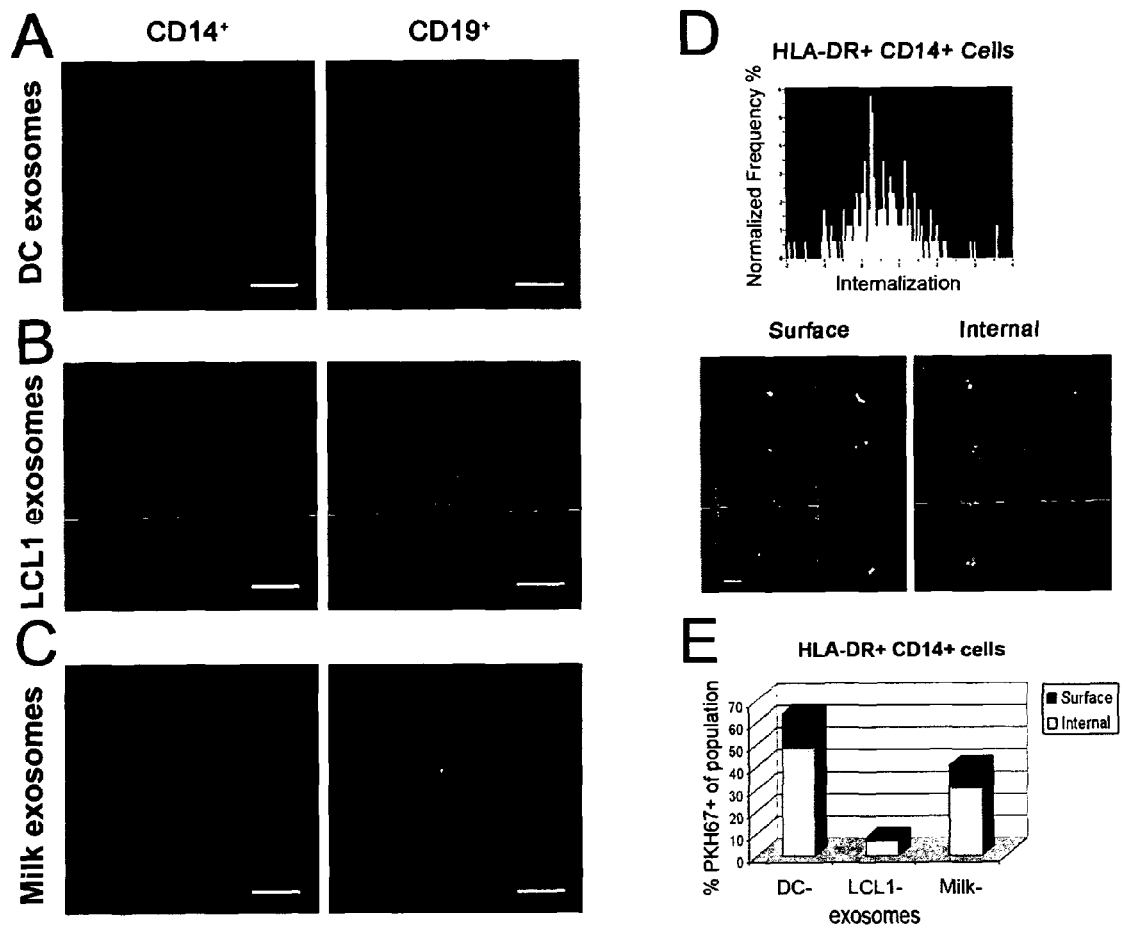
FIG. 5 Exosomes are mainly internalized by monocytes, whereas they associate to the cell membrane of B cells. PBMC were incubated for 4 h with PKH67 stained (A) DC-, (B) LCL1- and (C) breast milk-exosomes (10 µg of exosomes per 5×105 PBMC) and then stained for either anti-CD14 or anti-CD19, followed by Alexa Fluor 546 labeling, seen in red. The cells were analyzed by confocal laser scanning microscopy. As a background control the PKH67 dye pellet centrifuged in parallel was used, which showed undetectable fluorescence (data not shown). Scale bars represent 10 µm. Images of PBMC is shown as one representative experiment out of two. (D) ImageStream analysis shows that HLA-DR+ CD14+ cells mainly internalize exosomes. As an example a histogram for PKH67+ breast milk exosome (10 µg of exosomes per 5×105 PBMC) interaction with HLA-DR+CD14+ cells after 4 h is plotted. Composite images of cells with surface (<0), or internal (>0) exosomes are shown, HLA-DR (pink), CD14 (orange) and PKH67+ exosomes (green). The bar corresponding to 10 µm is shown in the lower left image. Results are shown as one representative experiment out of two using different blood donors. At least 104 total events were collected for each sample. (E) Percentages of exosomes associated with the HLA-DR+CD14+ cells as well as the percentages of those cells with internalized exosomes, which are calculated by the Internalization feature, are indicated in the inserted table. Two thousand events were analyzed with the Internalization feature.

Exosomes are Mainly Associated to the Cell Membrane of B Cells but are Internalized by Monocytes Next, we asked where the exosomes localize within the different cell types. We co-incubated PKH67 labeled exosomes with PBMC and analyzed exosome association by confocal laser scanning microscopy (CLSM). At 1 h, in general, no or only weak exosome signals could be detected in association with cells (data not shown), probably due to a lower detection level with CLSM compared to flow cytometry. After 4 h, DC exosomes were mainly internalized by monocytes (CD14$^+$), and to a lesser degree by B cells (CD19$^+$), which often had cell membrane associated exosomes (FIG. 5A). In contrast, LCL1 exosomes interacted to a higher degree with B cells, and were mainly localized to the cell membrane (FIG. 5B). Monocytes showed weaker signals for LCL1 B-cell exosomes (FIG. 5B). In general, milk exosomes showed weak signals, as seen in flow cytometry, and were either detected as internalized in monocytes or associated to the cell membrane of B cells (FIG. 5C). In the few cases where an interaction between exosomes and CD3$^+$ T cells occurred (approximately in one out of 50 cells), the exosomes were mainly localized near or in contact with the cell membrane (data not shown). Thus, these CLSM data are consistent with our flow cytometry data, showing that exosomes from EBV-transformed B cells preferentially target B cells, whereas DC-derived exosomes associate more with monocytes. However, these results do also suggest that exosomes interact differently with different cell types, where exosomes are mostly kept associated to the cell membrane of B cells and T cells, but internalized by monocytes.

To verify the association and localization of different exosomes with immune cells by another technical approach we decided to explore the ImageStream system. This system is a combined flow cytometer and fluorescence microscope that automatically captures multispectral images of each cell that passes through the flow cell at very high rates, enabling image-based analysis of large numbers of cells per sample. Using the internalization feature, we distinguished monocytes (HLA-DR$^+$CD14$^+$) that had surface associated exosomes, internalized exosomes, or both (intermediate; FIG. 5D). Due to technical reasons, no B cell data was obtained, but the monocyte data received was consistent with our conventional flow cytometry and CLSM data. The ImageStream showed that DC and milk exosomes preferentially associated with monocytes, while LCL1 exosomes did not (FIG. 5E). Furthermore, it was seen that the majority of the monocytes had internalized the various exosomes, reinforcing our previous findings (FIG. 5E). Hereby, we also show that this method is feasible for quantifying exosome localization in large numbers of cells.

Figure 6:
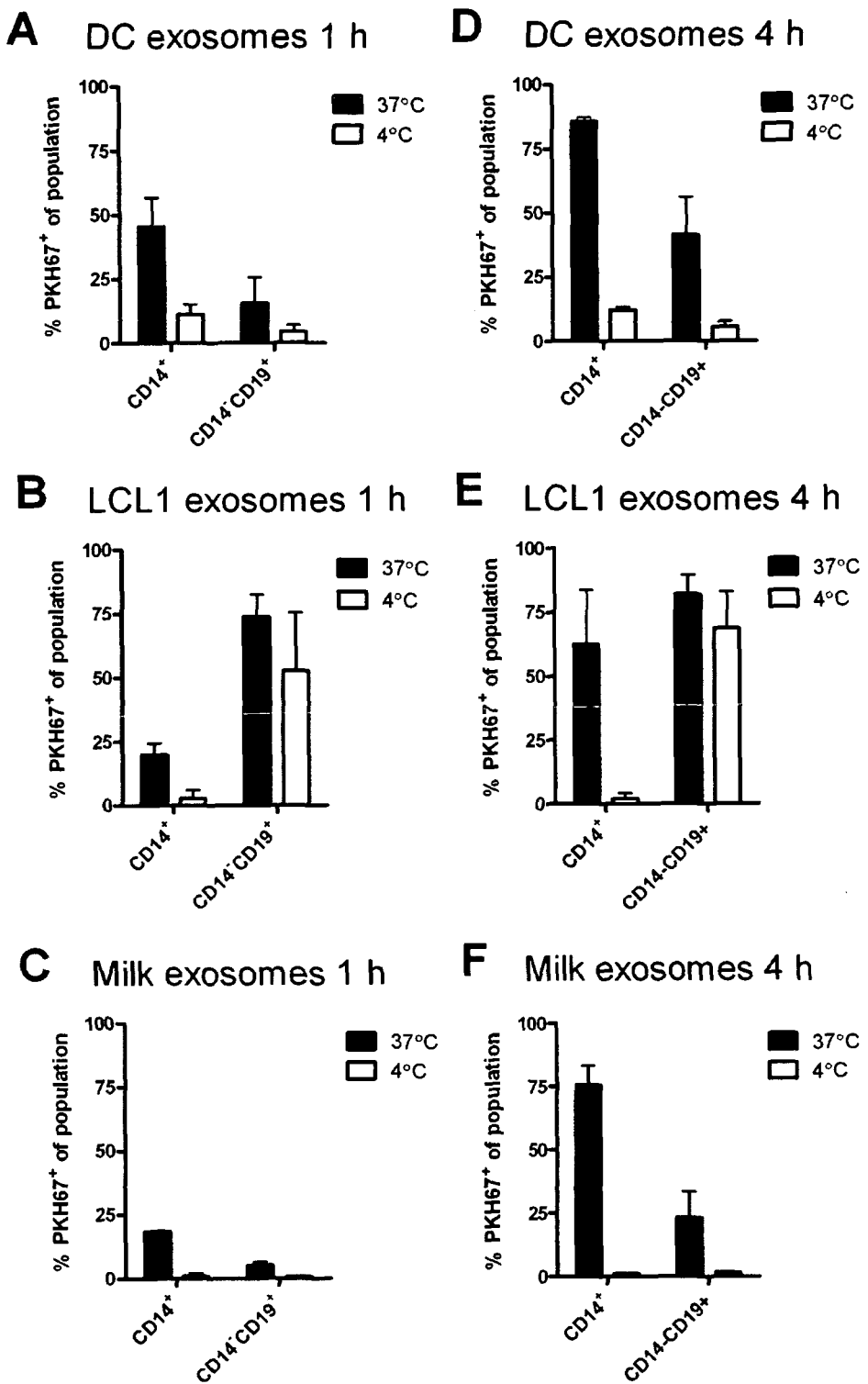
FIG. 6 The binding between LCL1-derived exosomes and B cells is temperature independent. PBMC were incubated with PKH67 labeled exosomes from DC, EBV transformed B cells or breast milk for 1 or 4 h at 37° C. or 4° C. and analyzed as described in FIG. 1. Bars represent percentages of exosome-positive cells within each sub-population of HLA-DR+ cells measured as PKH67+ signal by flow cytometry. Mean and s.d. for PBMC from three different donors are shown.

The Binding between LCL1-Derived Exosomes and B Cells is Temperature Independent To investigate whether the association of different exosomes with PBMC is receptor mediated or dependent on active internalization, we co-cultured PKH67$^+$ exosomes with PBMC at 4° C. and 37° C. For all three exosome types the association with monocytes decreased when incubation was performed at 4° C. for 1 and 4 h (FIG. 6A-F), indicative of an active, probably phagocytic, uptake by this cell type. DC (FIG. 6A and D) and milk exosome (FIG. 6C and F) associations with B cells were similarly diminished during cold conditions. In contrast, only a slight decrease in interaction between LCL1 exosomes and B cells was seen at 4° C. at both time-points (FIG. 6B and E). Thus, the interaction between LCL1 exosomes and B cells was largely temperature-independent and is therefore more likely mediated through adhesion molecules or surface receptors, why we set out to dissect this interaction further.

Figure 7:
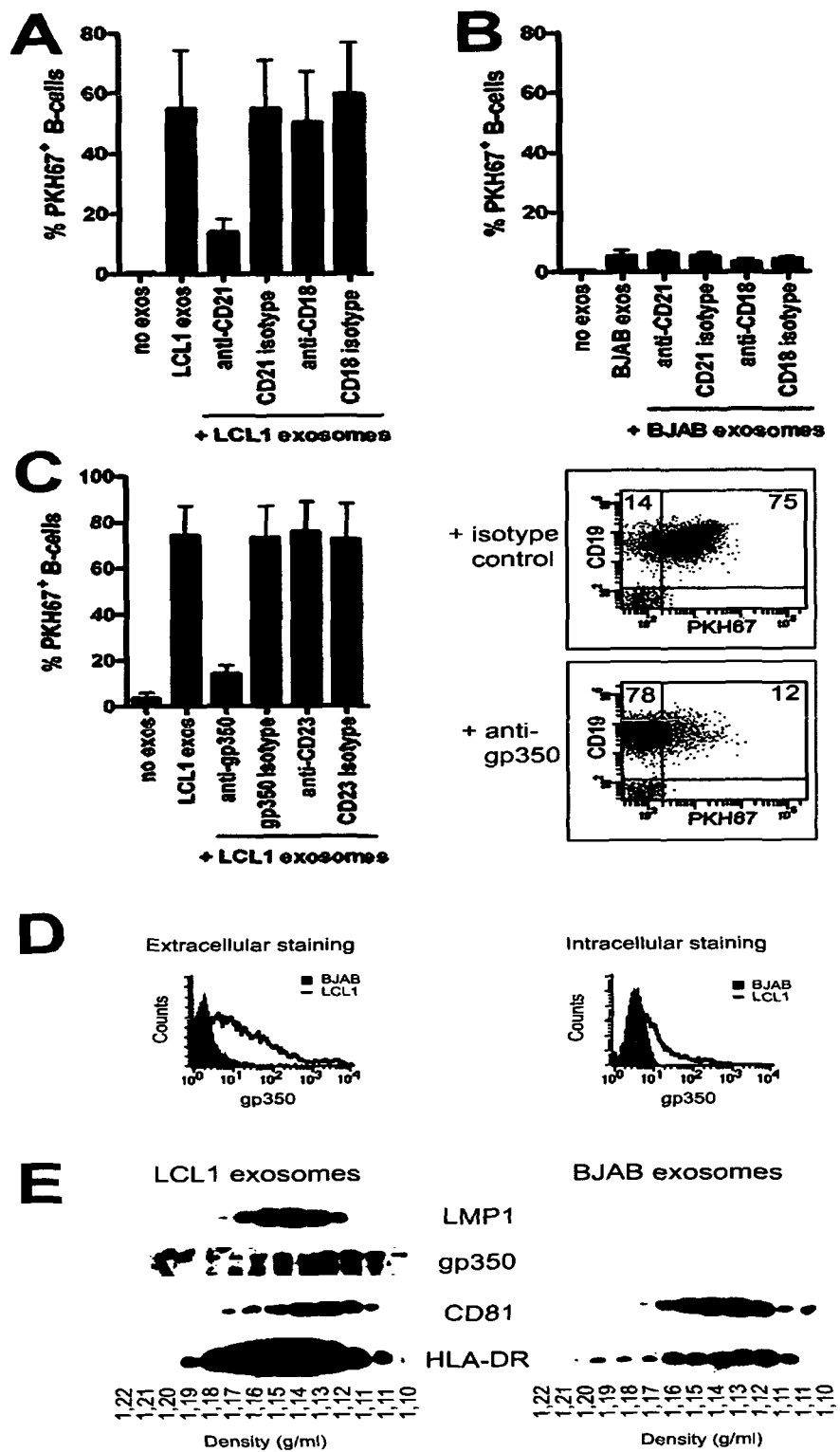
FIG. 7 The interaction between B cells and exosomes derived from EBV transformed B cells is mediated by interactions between CD21 and gp350. PBMC cultures were treated with anti-CD21, anti-CD18 or isotype-matched controls (20 µg/ml), before LCL1-exosomes (A) or BJAB-exosomes (B) were added for 4 h. (C) LCL1-exosomes were pre-incubated with anti-gp350 supernatant from the 72A1 mouse hybridoma (30% of total volume), anti-CD23 (30 µg/ml) or isotype-matched controls, and then added to purified B cells for 4 h. Representative flow cytometry dotplots, including percentage numbers, show LCL1-exosome association with B cells treated with isotype control (upper) or with anti-gp350 mAbs (lower). Analysis was performed as described in FIG. 1. Mean and s.d. for PBMC from three different donors are shown (A-C). (D) Flow cytometry histograms show extracellular- and intracellular expression of gp350, comparing BJAB cells (grey) with LCL1 cells (black line). Ten thousand cells were analyzed. (E) Pellets of sucrose gradient fractions from LCL1- and BJAB-exosome preparations were analyzed by immunoblot using Abs against LMP1, gp350, CD81 and HLA-DR (lower panel). The density of each fraction was determined by refraction index measurements. One representative experiment out of three is shown.

The Binding between LCL1-Derived Exosomes and B Cells is Dependent on CD21 Expressed on the B Cells B cells express cell surface receptors like the human complement receptor 2 (CD21), which together with a distinct pattern of adhesion molecules e.g. ICAM-1 or integrins, such as LFA-1 (CD11a/CD18), Mac-1 (CD11b/CD18) or p150,95 (CD11c/CD18), may mediate the observed strong B-cell preference of B-cell exosomes. To reveal the specificity of the exosome binding, mAbs against CD21 or CD18 were added to PBMC before incubation with exosomes. The interaction between LCL1 exosomes and peripheral blood B cells could efficiently be blocked by anti-CD21, whereas no blocking effect was observed with anti-CD18 Abs (FIG. 7A).

To elucidate whether the B-cell targeting observed was dependent on the EBV transformation of the B cells, we compared with exosomes from the EBV negative B cell line, BJAB. Results showed that BJAB exosomes bound to a 10 fold lower extent to B cells compared to LCL1 exosomes, suggesting the involvement of EBV-derived or -induced proteins in the binding (FIG. 7B). Taken together, these data indicate that the binding between LCL1 exosomes and B cells is dependent on an interaction with CD21 and not on LFA-1, Mac-1 or p150,95, and suggest a selective B-cell exosome targeting, which was specific for the exosomes derived from the EBV-transformed B cells.

gp350 on the LCL1-Exosomes Mediates the binding to B Cells

Next, we aimed to elucidate the exosomal ligand involved in the CD21 binding on B cells. Known ligands to CD21 include the low affinity receptor for IgE (CD23), the EBV envelope glycoprotein gp350 and the complement factor C3d. It has been shown that exosomes released from B cells and macrophages contain C3-fragments, but since heat inactivated fetal calf serum (FCS) was used in all our cell cultures, C3d is unlikely to make a difference here. CD23, which is highly expressed on EBV transformed B-cell lines was detected on our LCL1 exosomes but not on BJAB exosomes. The EBV glycoprotein gp350 is a lytic protein which is critical for viral attachment to B cells, but it has so far not been shown to be present on exosomes. Hence, gp350 and CD23 were our first candidates to be investigated for their possible involvement in the exosome-B-cell interaction. These ligands were blocked by either anti-gp350/220 or anti-CD23 Abs. The binding of LCL1 exosomes to B cells was substantially reduced when blocking gp350, but interestingly, no reduction in exosome binding was seen when CD23 was blocked (FIG. 7C). This observation suggests the presence of gp350 on the surface of LCL1 exosomes, and that this EBV protein mediates the exosome binding, and not CD23. As a control, we also added a non-neutralizing anti-gp350 mAb (2L10), which did not block exosome binding (data not shown), reinforcing the notion of a specific blocking of gp350 via the neutralizing mAb (72A1). The presence of gp350 in LCL1 cells was confirmed by flow cytometry analysis (FIG. 7D), and for exosomes in sucrose gradient by immunoblotting, where gp350 co-localized with HLA-DR and CD81 (FIG. 7E). These markers also partly co-localized with the EBV-encoded latent membrane protein 1 (LMP1), which has been previously found on exosomes. As expected, neither gp350 nor LMP1 were detected in the BJAB exosomes (FIG. 7E).

Exosome Signals are Derived from Exosomes and not Virions

Figure 8:
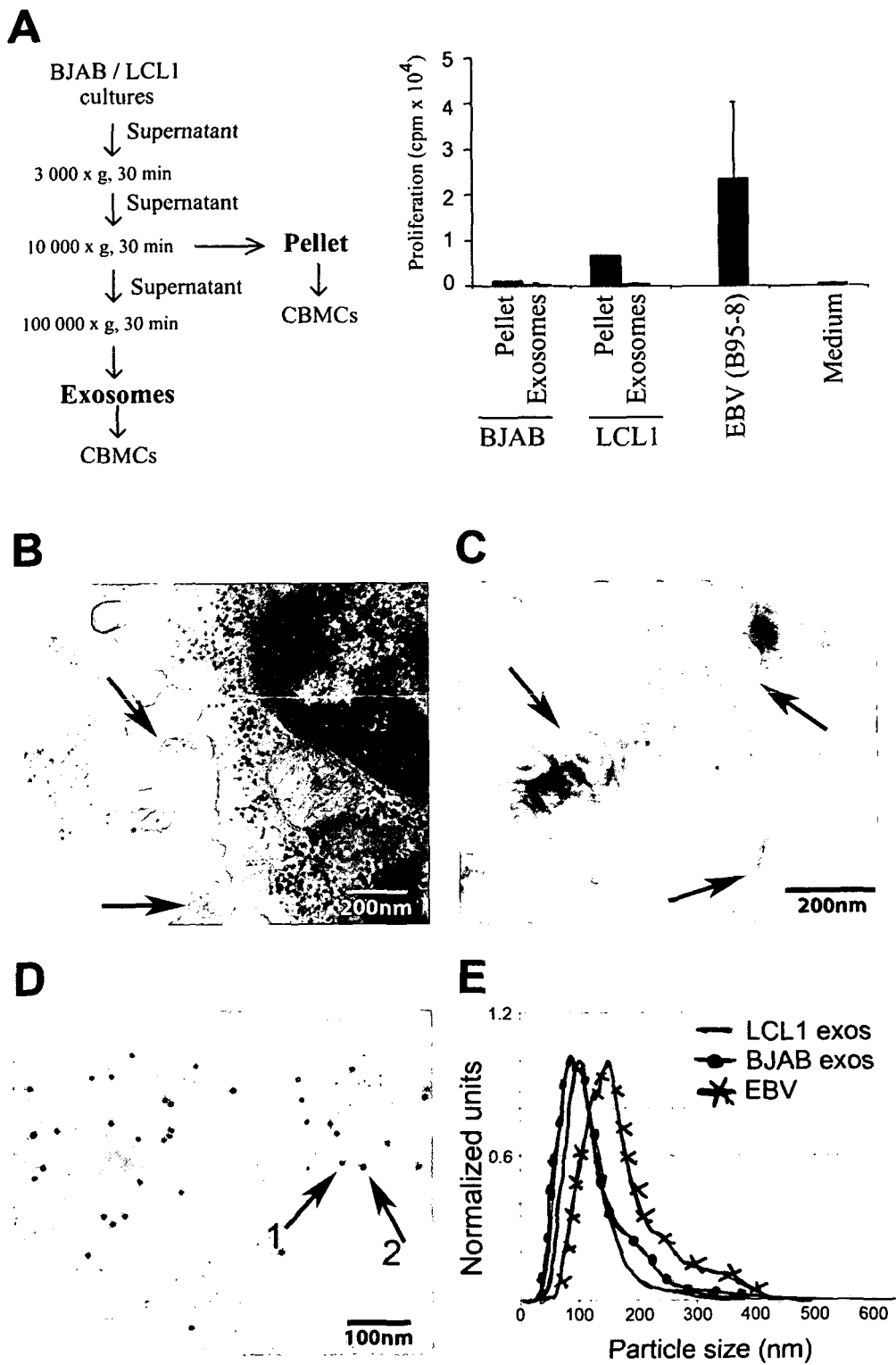
FIG. 8 Exosome signals are derived from exosomes and not virions. (A) To investigate the presence of infectious EBV in exosome preparations, the 10 000×g pellets as well as exosome preparations (100 000×g) from BJAB and LCL1 supernatants (SN) were added to cord blood mononuclear cells (CBMCs) and the outgrowth of LCLs was monitored by 3H-thymidine incorporation after 33 days. Supernatant from EBV-producing B95-8 cells served as a positive and cell culture medium alone as a negative control. The 10 000×g pellets from three different BJAB and LCL1 supernatant preparations were tested in one CBMC donor. Five different BJAB and LCL1 exosome preparations were tested in five different CBMC donors shown as mean values. (B) A representative image of exosomes associated to a B cell surface. (C) A TEM image shows LCL1 exosome preparations which have been processed by negative staining. Arrows in (B and C) indicate exosomes. (D) In immune EM, mAbs against CD63 (arrow 1) and HLA-DR (arrow 2) were added to LCL1 exosome preparations, and detected by gold-conjugated secondary Abs, 10 nm and 15 nm, respectively. (E) NanoSight measurement of particle size distribution in preparations from LCL1-exosomes, BJAB-exosomes and EBV. Data are shown as mean values (n=3) and are normalized to 1 for size-comparison.
Figure 9:
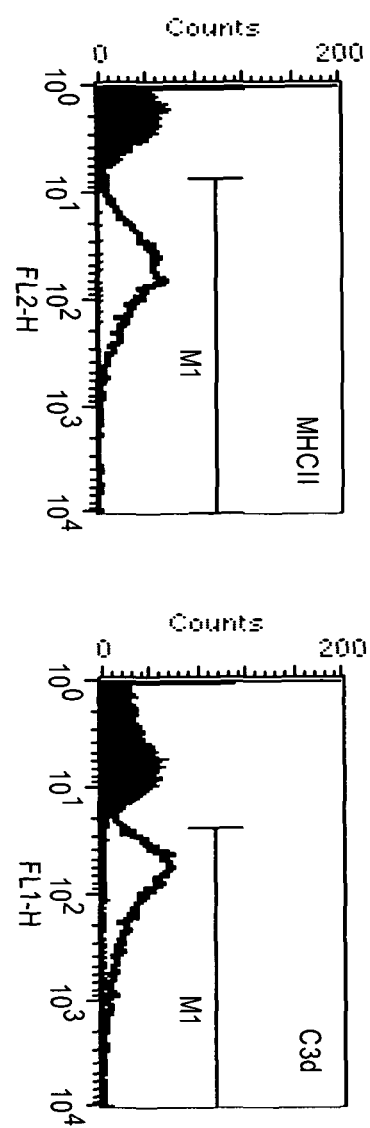
FIG. 9 Exosomes were prepared from the supernatant of the OVA pulsed bone marrow DC culture (OVAExo). For linking C3d on OVAExo the linker BS3 was mixed with C3d, followed by incubation for 30 min. Nonreacted reagent was removed by gel filtration and the elute containing C3d was added to the exosomes (C3dOVAExo). The reaction was stabilized using glycine.C3d linked Ova exosomes were incubated with anti-CD9 latex beads overnight. Exosomes were then labelled with (A) Anti-MHC class II or (B) Anti C3d antibodies conjugated to PE or FITC respectively, and analysed by FACS.
Figure 10:
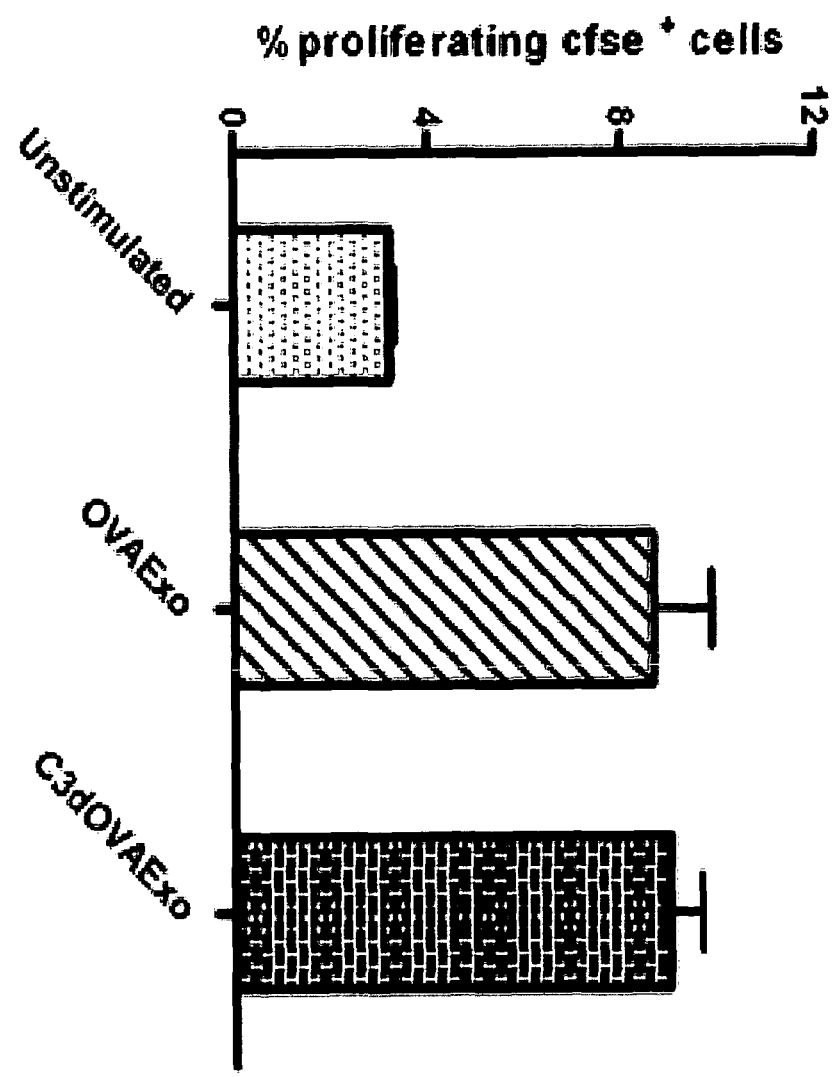
FIG. 10 Exosomes were prepared from the supernatant of the OVA pulsed Bone Marrow DC culture (OVAExo). For linking C3d on OVAExo the linker BS3 was mixed with C3d, followed by incubation for 30 min. Nonreacted reagent was removed by gel filtration and the elute containing C3d was added to the exosomes (C3dOVAExo). The reaction was stabilized using glycine. For in vitro proliferation assay, OVA TCR transgenic splenocytes (DO11.10) were labelled with cfse and coincubated with OVAExo or C3dOVAExo for five days at 370 C. Cfse dilution in the proliferating cells was analysed by flow cytometry.

The expression of gp350 on both LCL1 cells and exosomes raises the question whether some of our LCL1 cells are in a lytic stage of the EBV life cycle, which would implicate that EBV may also reside in the EBV transformed B-cell cultures as free virus particles. Therefore, there is a possibility that virions might contaminate our exosome preparations and thereby give a false positive signal for exosomes in our experiments. In preliminary experiments we detected viral DNA by PCR, however the presence of DNA does not always correspond to the presence of complete virions. Hence, the more sensitive cord blood assay was used to investigate the presence of infectious EBV virions, as well as TEM and immune EM analysis to detect EBV particles in our exosome preparations. The 10 000×g pellets (obtained during an intermediate centrifugation step during the exosome isolation procedure) as well as exosome preparations from BJAB and LCL1 supernatants were added to cord blood mononuclear cells (CBMCs) to monitor the outgrowth of EBV transformed primary B cells (FIG. 8A). Supernatants from the well-established EBV-producing marmoset B-lymphoblastoid cell line (B95-8) was used as a positive control. The addition of pooled 10 000×g pellets from BJAB supernatants did not induce the outgrowth of LCLs as quantified by $^3$H-thymidine incorporation. In addition, visual examination of the cultures did not reveal any typical aggregates of transformed B cells. In contrast, the addition of pooled 10 000×g pellets from LCL1 supernatants to the CBMCs induced the outgrowth of LCLs indicating the production of infectious virus particles by LCL1 cells. This finding is in line with the observed cell surface expression of gp350 on LCL1 cells (FIG. 7D), indicating that LCL1 cells are in a lytic, virus producing stage. However, no outgrowth of LCLs was observed after addition of exosome preparations (100 000×g) from BJAB and LCL1 supernatants to CBMCs, indicating the absence of infectious EBV within our LCL1 exosome preparations. Thus, all the virions produced by LCL1 are pelleted down during the 10 000×g centrifugation step. In addition, we investigated by TEM and immune EM whether exosome preparations from LCL1 cells contain any pleiomorphic EBV particles, a general characteristic for herpes viruses. Neither exosomes attached to primary B cells (FIG. 8B) nor exosome preparations alone (FIGS. 8C and D) revealed any EBV particles in the size of infectious EBV (200 nm) or naked high-density virus capsids. Only vesicles of approximately 100 nm were seen, where the majority were labelled with CD63 and HLA-DR, indicative of exosomes (FIG. 8C). These results are also in line with our findings with Immunoblot, where gp350 co-localized with HLA-DR and CD81 (FIG. 7E). The size distribution was further investigated by nanoparticle tracking analysis (NTA; NanoSight). This method quantitatively confirmed the lower size range within the LCL1- and BJAB-exosome preparations, having an average around 100 nm, compared to EBV, which had a top at above 150 nm (FIG. 8E), further supporting the absence of virions in our exosome preparations.

Discussion

It is known that different cell types produce exosomes with phenotypes that mainly reflect their cells of origin. Here we looked at the other side of the exosome communication pathway and demonstrated that the exosomes tested, both from MDDCs and breast milk, seem to have the same main target in human peripheral blood, i.e. monocytes. Reaching the monocytes, the exosomes seem to be actively engulfed, probably by phagocytosis, which has also recently been demonstrated to be the mechanism of exosome uptake by other phagocytes such as macrophages. However, this also shows that the selectivity of exosomes to target monocytes may change if the exosome producing cell carries pathogen-specific molecules, which we here demonstrated by comparing exosomes from an EBV negative (BJAB) with an EBV positive B-cell line (LCL1). The LCL1-derived exosomes were mainly targeting B cells, but this was not seen for the BJAB exosomes. The interaction between LCL1 exosomes and B cells was efficiently blocked by either Abs to CD21 on B cells or to gp350 on exosomes, but neither by anti-CD18 nor anti-CD23, demonstrating the involvement of EBV. Why anti-CD23 had no effect on the cell-exosome interaction, even though CD23 is more abundant on LCL1 compared to BJAB, could be due to a lower affinity interaction between CD23 and CD21 compared to the gp350-CD21 interaction. This indicates that a very high molecular affinity is needed for a rapid (1 h) binding of exosomes in vitro, possibly being even more important in vivo.

The interaction of the various exosomes with T cells was rather low (less than 8% of T cells positive for exosomes), even though DC and B-cell exosomes are known to display the intercellular adhesion molecule (ICAM)-1 which binds to LFA-1 expressed on e.g. T cells.

The observation that we had gp350 on the LCL1 exosomes raised the question whether we had infectious and/or pleiomorphic EBV particles in our exosome preparations, which could be responsible for the PKH67 signal seen on B cells. The binding of EBV to CD21 is well established. By using the sensitive cord blood transformation assay as well as TEM analysis (FIG. 8B-D) we did not find any evidence for virions in our exosome preparations. Thus, it seems like that the samples were cleared of virions by centrifugation and therefore, we consider it unlikely that virions should be responsible for fluorescence signal seen on B cells.

Our novel finding of targeted B-cell inter-communication via gp350-harboring exosomes might also reflect the situation in vivo. Gp350-harboring exosomes may be secreted in asymptomatic carriers of EBV and we speculate that the binding of exosomes to uninfected B cells may lower the efficiency of virion binding, and hence infection, by blockade of the EBV entry receptor, CD21. In the present study we also observed that the EBV transformed B cells seemed to produce more exosomes, measured as protein concentration, compared to the EBV negative B cells. This may also mirror the situation in vivo, where a high number of exosomes may contribute to control the spread of EBV infection. Alternatively, the induction of exosome production and the exosomal expression of gp350 may contribute to the immune modulatory potential of EBV.

Our findings also suggest how exosomes can be engineered, e.g. by inducing the expression of gp350, to redirect their cellular targeting to B cells, which may potentiate their therapeutic usefulness. A role for B cells in producing a complete T-cell response was suggested already in the eighties. Furthermore, B cells are particularly important in achieving long term T-cell immunity and recently, we have shown that exosomes require the support of activated B cells for generating antigen specific T-cell responses in vivo. Hence, by targeting B cells in cancer vaccines, tolerance could be broken and a more long-lasting T cell immunity might be achieved. Furthermore, CD21 is not only expressed by B cells, but also by follicular dendritic cells (FDCs). This implies that exosomes with surface-associated gp350 may also target FDCs in vivo, thereby enhancing a possible immune activation and memory in vivo.

In conclusion, the inventors have shown that exosomes, found in breast milk, produced by human monocyte derived DC and an EBV negative B cell line, do not preferably associate to B cells. Instead, they mainly target monocytes, which actively engulf exosomes, as demonstrated for milk and DC exosomes. However, if B cells harbor EBV in its lytic stage, the produced exosomes change their preference from monocytes towards B cells, whereby exosome associated gp350 binds to the EBV entry receptor, CD21, on B cells. Exosomes derived from EBV transformed B cells might have a role in reducing viral uptake by B cells during EBV infection. Furthermore, exosomes targeting B cells could potentially be efficient in inducing long term immune responses of both the cellular and humoral type, and hence they should be considered as potential tools in the treatment of cancer and inflammatory diseases.

Clincal Protocol

The administration of antigen-loaded ETBT exosomes or antigen-loaded DC exosomes or antigen-loaded CD40-stiulated B cell exosomes to cancer patients can be carried out as described by B Escudier et al., supra.

Model Study

According to the invention EBV-derived glycoprotein gp350 on exosomes is specifically targeting human B cells via CD21 in vitro. The inventors of present invention have also seen in the mouse model, that B cell activation is needed for a strong OVA (ovalbumin) loaded exosome-induced T cell responses). Therefore, the model study is aimed at testing whether targeting B cells with exosomes bearing gp350 via CD21 can facilitate B cell activation and induce T cell responses in vitro and in vivo. Since gp350 does not bind to mouse CD21 due to steric hindrance, an alternative model is used in the murine system.

C3d is 35 kDa protease resistant fragment of the complement factor C3 and is generated in the course of complement activation. A number of studies have shown that C3d can be used as a molecular adjuvant as CD21 on B cells binds C3d-tagged antigen, which leads to cross-linking of the BCR with CD19, thereby reducing the threshold for B cell activation as well amplify the magnitude of the signal. CD21 causes a model antigen that is artificially tagged with three copies of C3d to be immunogenic at a concentration that was 0.001% of that of the least immunogenic dose of unmodified antigen. The role of C3d can be summarized as follows—

Targeting of antigen to the CD21 (CR2) by C3d tagging results in increased Ag processing and Ag presentation in all B cells and FDC Crosslinking between CD21 and BCR results in the full activation of Ag-specific B cells C3d-tagged antigens are captured by FDC in the spleen and remain bound to the cell surface for extended periods of time, generate and maintain memory B cells.

C3d can increase the in vivo lifespan of antigens by forming multimers with the antigen or by acting as protein carrier Experimental Procedure of Model Study:

BMDC Culture:

BMDCs (Bone marrow dendritic cells) were generated from bone marrow stem cells in the presence of IL-4 and 10% GM-CSF conditioned medium (Ag8653/X63 clone). At day 6, 50% of the culture supernatant was replaced with fresh medium. For OVA loading on exosomes, 300 µg OVA proteins were added to DC cultures at day 6 and incubated ON followed by washing once and then LPS was added to the culture. After 48 h, exosomes (OVAExo) were purified from the culture supernatant by ultracentrifugation.

Preparation of Exosomes from DC (Dendritic Cells) Culture Supernatants

The culture supernatants were subjected to centrifugation at 3.000×g, followed by 10.000×g for 30 min. Exosomes were pelleted at 100.000×g for 2 h and washed at 100.000×g. Pelleted exosomes were dissolved in PBS. The protein contents were measured by a DC protein assay (Biorad).

Phenotypic Analysis of Exosomes by FACS

Ten micrograms of exosomes were incubated with 10 µl of aldehyde/sulfate latex beads previously coated with anti-CD9 antibodies, rotated over night (ON) at room temperature (RT). The reaction was stopped by 1 ml 100 mM glycine (Sigma). Beads with exosomes were labeled with a panel of FITC or PE conjugated antibodies specific for H-2Kd, CD9, CD54, CD80, CD81, CD86, C3d (BD Biosciences, San Jose, Calif., USA) and the corresponding isotype matched antibodies.

C3d Linking on OVAExo:

For linking C3d on OVAExo the linker BS3 was mixed with C3d, followed by incubation for 30 min. Nonreacted reagent was removed by gel filtration and the elute containing C3d-BS3 was added to the exosomes (C3dOVAExo). The reaction was stabilized using glycine.

DO11.10 CD4+ T Cell Isolation and In Vitro T Cell Proliferation Assay

DO11.10 splenocytes were stained with 5µM CFSE (Carboxy Fluoroscein Succinimidyl Ester) for 15 min at 370C. Labeling was stopped by adding cold PBS/10% FCS. Cells were then washed 3× in PBS and co-cultured at a concentration of 1×106 cells/ml with of Pep-Exo, OVA-Exo and the respective controls followed by incubation at 37° C. in a humid incubator with 5% CO2 for 5 days.

In vivo T cell proliferation assay

Splenocytes from DO11.10 mice were adoptively transferred to BALB/c mice i.v. with 5.5×106 cells/mouse at day 0. On day 1, mice were immunized i.v. with C3dOVAExo, OVAExo or with respective PBS control. On day 4, mice were sacrificed and splenocytes were stained with anti-CD3-APC together with anti-CD4-PE anti-KJ1-26+-FITC antibodies specific for OVA TCR and the number of KJ1-26+-cells assessed by FACS. Lymphocyte early activation was also checked using anti-CD69 and anti-CD25 antibodies by FACS.

Determination of Serum Antibody Levels by ELISA

To determine specific antibody responses, microtiter plates were coated with 10 µg/ml of OVA protein and incubated ON followed by incubation with serial dilutions of sera ON. Isotypes of the reactive antibodies were determined by incubating for 2 h at RT with alkaline phosphatase-conjugated goat immunoglobulin specific for mouse µ and γ isotypes. Development was done at RT with p-nitrophenyl phosphate disodium and the absorbance was measured at 405 nm at different time points by an ELISA reader. Usually, for the treatment purpose the quantity of exosomes produced per process was evaluated in terms of the amount of MHC class II molecules by adsorption ELISA. The adsorption ELISA assay was evaluated by calculating the total number of MHC class II molecules associated with Raji cells and immature day 7 MDDCs to be approximately 1.0 and $5.5 \times 10^6$ MHC class II molecules per cell, respectively. Inflammatory stimuli induce accumulation of MHC class II complexes on dendritic cells. The GMP process allowed to harvest about $5 \times 10^{14}$ exosomal MHC class II molecules.

Conclusions

In conclusion, these results show that exosomes linked to C3d are more efficient in inducing T cell responses via activation of native B-cells compared to exosomes without C3d in vivo in the murine system. This suggests that in humans, gp350-expressing exosomes, which targets the same molecule as C3d, also will be more efficient in inducing T cell responses via antigen presentation of B-cells compared to exosomes not expressing gp350.

All prior art documents referred to in the description of the present invention and of preferred embodiments thereof are incorporated herein by reference.

In specific embodiments the invention also relates to the following items:

1. A method of treating cancer in a person by eliciting an immune response to an antigen displayed on cancerous cells of the patient, comprising:
   (a) Providing a sample of peripheral blood from the person;
   (b) Isolating B cells from the sample;
   (c) Infecting the isolated B cells with Epstein Barr virus (EBV);
   (d) Transforming the infected B cells to a latent stage;
   (e) Culturing the EBV transformed B cells in the presence of cancer antigen;
   (f) Harvesting exosomes released from the EBV transformed B cells;
   (g) Administering the harvested exosomes to the patient to elicit said immune response.

2. A method of treating cancer in a person by eliciting an immune response to an antigen displayed on cancerous cells of the patient, comprising:
   (a) Providing a sample of peripheral blood from the person;
   (b) Isolating B cells from the sample;
   (c) Infecting the isolated B cells with Epstein Barr virus (EBV);
   (d) Transforming the infected B cells to a latent stage;
   (e) Culturing the EBV transformed B cells;
   (f) Harvesting exosomes released from the EBV transformed B cells;
   (g) Contacting the harvested exosomes with cancer antigen to produce antigen loaded exosomes;
   (h) Administering the cancer antigen loaded exosomes to the patient to elicit said immune response.

3. The method of item 1 or 2, comprising neutralizing latent membrane protein 1 (LMP-1) on the exosomes.

4. The method of item 3, wherein the neutralizing agent comprises a Fab-fragment molecule.

5. A method of treating cancer in a person by eliciting an immune response to an antigen displayed on cancerous cells of the patient, comprising:
(a) Providing a sample of peripheral blood from the person;
(b) Isolating monocytes from the sample;
(c) Culturing the monocytes to immature dendritic cells;
(d) Modifying the immature dendritic cells to express a CD21-binding moiety;
(e) Contacting the modified immature dendritic cells with a cancer antigen to transform them into cancer antigen loaded mature dendritic cells;
(f) Harvesting cancer antigen loaded dendritic cell exosomes released from the mature dendritic cells;
(g) Administering the cancer antigen loaded dendritic cell exosomes to the patient to elicit said immune response.

6. The method of item 5, wherein the CD21-binding protein moiety comprises one or several of: gp350, EBV gp350/220 (gp350 (470t), CD23, C3b, iC3b, C3d, IFN-alpha.

7. A method of treating cancer in a person by eliciting an immune response to an antigen displayed on cancerous cells of the patient, comprising:
(a) Providing a sample of peripheral blood from the person;
(b) Isolating B cells from the sample;
(c) Culturing the B cells;
(d) Modifying the B cells to express a CD21-binding moiety;
(e) Contacting the modified B cells expressing a CD21-binding moiety with a cancer antigen;
(f) Harvesting cancer antigen loaded exosomes released from the cancer antigen-contacted modified B cells;
(g) Administering the cancer antigen loaded B cell exosomes to the patient to elicit said immune response.

8. The method of item 7, wherein the CD21-binding protein moiety comprises one or several of: gp350, EBV gp350/220 (gp350 (470t), CD23, C3b, iC3b, C3d, IFN-alpha.

9. A method of treating cancer in a person by eliciting an immune response to an antigen displayed on cancerous cells of the patient, comprising:
(a) Providing a sample of peripheral blood from the person,
(b) Isolating B cells from the sample;
(c) Culturing the B cells;
(d) Modifying the B cells to express a CD21-binding moiety;
(e) Harvesting exosomes released from the CD 21-binding moiety expressing B cells;
(f) Contacting the harvested exosomes with a cancer antigen to produce cancer antigen loaded exosomes;
(g) Administering the cancer antigen loaded B cell exosomes to the patient to elicit said immune response.

10. The method of item 9, wherein the CD21-binding protein moiety comprises one or several of: gp350, EBV gp350/220 (gp350 (470t), CD23, C3b, iC3b, C3d, IFN-alpha.

11. A method of producing a cancer antigen loaded exosome, the method comprising any of: step (a) through step (f) of claim 1; step (a) through step (g) of claim 2; step (a) through step (f) of claim 5; step (a) through step (f) of claim 7; step (a) through step (f) of claim 9.

12. An exosome obtained or obtainable by the method of item 11.

13. A cancer vaccine comprising the exosome of item 12.

14. A T cell stimulated in vitro by the exosome of item 12.

15. A B-cell or dendritic cell (DC) exosome comprising a CD21-binding moiety.

16. The exosome of item 15, wherein the CD21-binding moiety is selected from gp350, EBV gp350/220 (gp350 (470t), CD23, C3b, iC3b, C3d, IFN-alpha.

The invention claimed is:

1. A method for producing specific immune modulating exosomes, comprising:
(i) transforming B-cells by infecting latent stage B-cells with Epstein Barr virus, to thereby express gp350 capable of binding to the CD 21 receptor of a native B-cell;
(ii) culturing the transformed B-cells;
(iii) harvesting exosomes released from the transformed B-cells, wherein the exosomes comprise one or more moieties capable of binding to a native B-cell; and wherein the exosomes are directly and/or indirectly loaded with one or more antigens and/or immunosuppressing agents, wherein the one or more antigens are selected from the group consisting of one or more cancer antigens, one or more viral antigens, one or more bacterial antigens, one or more immunosuppressive agents, and combinations of any two or more thereof.

2. The method according to claim 1, wherein the method further comprises neutralizing any latent membrane protein 1 (LMP-1) on the exosomes.

3. The method according to claim 2, wherein the neutralizing of LMP-1 is accomplished with Fab-fragment molecules.

4. The method according to claim 1, wherein the one or more cancer antigens are selected from the group consisting of one or more antigens expressed on the surface of a tumour cell or antigenically active fragment thereof, a tumour antigen peptide fragment comprising from 8 to 12 amino acid residues or from 15 to 24 amino acid residues capable of stimulating T cells, a tumour cell lysate, and combinations of any two or more thereof.

5. The method according to claim 1, wherein the exosomes are indirectly loaded by co-culturing the transformed B-cells in the presence of one or more antigens and/or one or more immunosuppressive agents.

6. The method according to claim 1, wherein the exosomes are directly loaded by contacting the harvested exosomes with one or more antigens and/or one or more immunosuppressive agents, and, optionally, changing the pH or chemically linking the one or more antigens and/or one or more immunosuppressive agents to the exosomes.

7. The method according to claim 1, wherein the one or more antigens are autogenic and/or allogenic.

8. The method according to claim 1, wherein the exosomes are loaded with a number of antigens selected from the group consisting of 2, 3, 4, 5, 6, and more than 6.

9. A method according to claim 1, wherein the transformed cells are cultured for a period of time selected from the group consisting of 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, and 6 months.

10. The method according to claim 1, wherein the exosomes are harvested at a time interval selected from the group consisting of every two days, every third day, every fourth day, every fifth day, every sixth day and every seventh day.

11. A method according to claim 1, wherein the yield of exosomes is selected from the group consisting of at least about 0.2 µg exosomes/1 million EBTB cells, at least about 0.3 µg exosomes/1 million EBTB cells, at least about 0.4 µg exosomes/1 million EBTB cells, at least about 0.5 µg exosomes/1 million EBTB cells, at least about 0.6 µg exosomes/1 million EBTB cells, at least about 0.7 µg exosomes/1 million EBTB cells, at least about 0.8 µg exosomes/1 million EBTB cells, at least about 0.9 μg exosomes/1 million EBTB cells, at least about 1.0 μg exosomes/1 million EBTB cells, at least about 1.5 μg exosomes/1 million EBTB cells, at least about 2.0 μg exosomes/1 million EBTB cells, at least about 2.5 μg exosomes/1 million EBTB cells, at least e.g. about 3.0 μg exosomes/1 million EBTB cells, at least about 5.0 μg exosomes/1 million EBTB cells, and at least about 10.0 μg exosomes/1 million EBTB cells, during a time period of about 48 hours of culture of EBTB cells.

12. A method according to claim 1, wherein the exosomes are harvested and collected by ultracentrifugation or differential centrifugation or any combination thereof, pelleted exosomes are collected, and, optionally, collected pelleted exosomes are washed with a suitable medium.

* * * * *